US012773398B1

(12) United States Patent
Druzgala et al.

(10) Patent No.: US 12,773,398 B1
(45) Date of Patent: Oct. 27, 2026

(54) FORMULATIONS OF CRYSTALLINE BUDIODARONE FORM-1

(71) Applicant: Xyra, LLC, Los Altos, CA (US)

(72) Inventors: Pascal Druzgala, Santa Rosa, CA (US); Cyrus Becker, Pleasanton, CA (US)

(73) Assignee: Xyra, LLC, Los Altos, CA (US)

(*) Notice: Subject to any disclaimer, the term of this patent is extended or adjusted under 35 U.S.C. 154(b) by 0 days.

(21) Appl. No.: 19/382,796

(22) Filed: Nov. 7, 2025

(51) Int. Cl.

| | |
|---|---|
| ***A61K 31/343*** | (2006.01) |
| ***A61K 9/20*** | (2006.01) |
| ***A61K 9/48*** | (2006.01) |
| ***A61K 9/50*** | (2006.01) |
| ***A61K 9/51*** | (2006.01) |

(52) U.S. Cl.
CPC .......... *A61K 31/343* (2013.01); *A61K 9/2027* (2013.01); *A61K 9/2054* (2013.01); *A61K 9/4858* (2013.01); *A61K 9/4866* (2013.01); *A61K 9/5026* (2013.01); *A61K 9/5123* (2013.01); *A61K 9/5161* (2013.01)

(58) Field of Classification Search
CPC .................................................... A61K 31/343
See application file for complete search history.

(56) References Cited

U.S. PATENT DOCUMENTS

| | | | |
|---|---|---|---|
| 5,364,880 A | 11/1994 | Druzgala | |
| 6,372,783 B1 | 4/2002 | Druzgala et al. | |
| 6,818,782 B2 | 11/2004 | Druzgala et al. | |
| 7,037,933 B2 | 5/2006 | Druzgala | |
| 7,351,842 B2 | 4/2008 | Druzgala | |
| 7,498,449 B2 | 3/2009 | Druzgala et al. | |
| 9,549,912 B2 | 1/2017 | Milner et al. | |
| 11,759,640 B2 | 9/2023 | Druzgala et al. | |
| 11,839,768 B2 | 12/2023 | Druzgala et al. | |
| 11,975,202 B2 | 5/2024 | Druzgala et al. | |
| 12,115,373 B2 | 10/2024 | Druzgala et al. | |
| 12,257,228 B2 * | 3/2025 | Druzgala | A61K 31/444 |
| 2005/0154216 A1 | 7/2005 | Druzgala et al. | |
| 2011/0136779 A1 * | 6/2011 | Milner | A61K 31/4545 514/357 |
| 2011/0144199 A1 | 6/2011 | Milner et al. | |
| 2011/0269762 A1 | 11/2011 | Milner et al. | |
| 2013/0143861 A1 | 6/2013 | Milner et al. | |
| 2014/0309296 A1 | 10/2014 | Druzgala | |
| 2017/0354635 A1 | 12/2017 | Milner et al. | |
| 2023/0372284 A1 | 11/2023 | Druzgala et al. | |

FOREIGN PATENT DOCUMENTS

| | | | |
|---|---|---|---|
| EP | 1857450 | A1 | 11/2007 |
| WO | 2001029018 | A3 | 11/2001 |
| WO | 02/102788 | A1 | 12/2002 |
| WO | 2003050102 | A1 | 6/2003 |
| WO | 2002038557 | A9 | 9/2003 |
| WO | 2005099684 | A1 | 10/2005 |
| WO | 2007011835 | A3 | 3/2007 |
| WO | 2014143525 | A1 | 9/2014 |
| WO | 2014143625 | A1 | 9/2014 |
| WO | 2023133510 | A1 | 7/2023 |
| WO | 2025010071 | A1 | 1/2025 |

OTHER PUBLICATIONS

Ang, Yen-Sin, et al. "A new therapeutic framework for atrial fibrillation drug development." Circulation Research 127.1 (2020): 184-201.
Arya A, Silberbauer J, Teichman SL, Milner P, Sulke N, Camm AJ. A preliminary assessment of the effects of ATI-2042 in subjects with paroxysmal atrial fibrillation using implanted pacemaker methodology. EP Europace. 2009;11(4):458-64.
"Arya et al: ""P2-76"", Heart Rhythm, Elsevier, US, vol. 3, No. 5, May 1, 2006 (May 1, 2006), p. SI64, XP005483785, ISSN: 1547-5271, DOI: 10.1016/J.HRTHM.2006.02.488 abstract".
Ezekowitz MD, Nagarakanti R, Lubinski A, Bandman O, Canafax D, Ellis DJ, et al. A randomized trial of budiodarone in paroxysmal atrial fibrillation. Journal of Interventional Cardiac Electrophysiology. 2012;34(1):1-9.
Ezekowitz, M. D., Dimarco, J., Kaszala, K., Ellenbogen, K., Boddy, A., & Koren, A. A placebo-controlled, double-blind, randomized, multicenter study to assess the effects of dronedarone on atrial fibrillation burden in subjects with permanent pacemakers. J Interv Card Electrophysiol (2015) 42:69-76.
Hadjittofis, Eftychios, et al. "Influences of crystal anisotropy in pharmaceutical process development." Pharmaceutical research 35.5 (2018): 100.
Juhasz, A., & Bodor, N. (2000). Cardiovascular studies on different classes of soft drugs. Die Pharmazie, 55(3), 228-238.
Munger, T. M.; Wu, L. Q.; Shen, W. K. Journal of Biomedical Research. 2014, 28 (1): 1-17. doi:10.7555/JBR.28.20130191. PMC 3904170. PMID 24474959.
Trebbin, Martin, et al. "Anisotropic particles align perpendicular to the flow direction in narrow microchannels." Proceedings of the National Academy of Sciences 110.17 (2013): 6706-6711.
Wikipedia contributors. "Dissolution testing." Wikipedia, The Free Encyclopedia. Wikipedia, The Free Encyclopedia, Dec. 9, 2023. Web. Dec. 12, 2025.
You, Hye-Su, et al. "Amiodarone-induced multi-systemic toxicity involving the liver, lungs, thyroid, and eyes: a case report." Frontiers in Cardiovascular Medicine 9 (2022): 839441.
Zhang, Huixiang, et al. "Prevention of crystal agglomeration: Mechanisms, factors, and impact of additives." Crystals 14.8 (2024): 676.
U.S. Appl. No. 63/804,515, filed May 12, 2025.

(Continued)

*Primary Examiner* — Rei Tsang Shiao
(74) *Attorney, Agent, or Firm* — Banner & Witcoff, Ltd.

(57) ABSTRACT

Provided here is a composition comprising a stable, flowable, agglomeration-resistant, granular composition of a crystalline salt of budiodarone. Also provided are methods of manufacturing such stable, flowable, agglomeration-resistant granular compositions.

26 Claims, 8 Drawing Sheets

(56) References Cited

OTHER PUBLICATIONS

Zhang, Ke, et al. "Specific surface area of mannitol rather than particle size dominant the dissolution rate of poorly water-soluble drug tablets: A study of binary mixture." International Journal of Pharmaceutics 660 (2024): 124280.

Sep. 3, 2026—(WO) Invitation to Pay Additional Fees, Written Opinion of the International Searching Authority, and Partial International Search Report—App. PCT/US26/27631.

Caira, Mino R., Crystalline Polymorphism of Organic Compounds, Topics in Current Chemistry, vol. 198 (1998), pp. 163-208.

* cited by examiner

FORMULATIONS OF CRYSTALLINE BUDIODARONE FORM-1

1. FIELD

This disclosure provides for rapid-release pharmaceutical formulations comprising a crystalline budiodarone salt. In some embodiments, the disclosed formulations are provided in capsules and tablets for oral delivery. In some embodiments, the capsules and tablets so formed exhibit dissolution rates that achieve more than 50% release in a standard dissolution test and preferably more than 70% dissolution in 30 minutes and even more preferably, more than 75% of budiodarone dissolution in 30 minutes in said standard test.

2. BACKGROUND

Amorphous budiodarone was first prepared as its free base and recovered as an oil. As a free base, the compound lacked long term stability. U.S. Pat. No. 9,954,912 (the '912 patent) disclosed that a budiodarone tartrate salt could be crystallized using isopropanol/water as a co-solvent (15:1 by weight). The X-ray diffraction (XRD) pattern for this structure is provided in FIG. 1A, which is designated as "Form-1". As illustrated in FIG. 1B, these crystals have a short, needle-like structure, which is known in the art to require formulation techniques compatible with such crystal structures when formulation for capsules and tablets.

An additional requirement involves meeting a standardized requirement that at least 80% of the active drug must be released from the capsule or tablet within 1 hour in a simulated gastric fluid. As such, the approaches used to formulate crystalline budiodarone tartrate into compositions that are compatible with capsule and tableting instruments must also meet this test.

It is also important that the release of the active drug not be backloaded into the latter 30 minutes of the test period. While releasing a majority of the required 80% of the active in the last 30 minutes of the test period will meet this test requirement, it can have the unwanted result of a delayed onset to Cmax after ingestion. Such would be inconsistent with providing the patient with the early onset of therapeutic effectiveness. It is also important that release rates are sufficiently robust to account for the serum half-life of the drug and also to ensure that each batch of the formulation will reproducibly conform to this requirement.

In the case of crystalline budiodarone tartrate, the generation of a formulation that has a quick release of the active drug would be beneficial.

3. SUMMARY

Disclosed are granular pharmaceutical formulations suitable for filling capsules or compressing into tablets, which formulations comprise a crystalline salt of budiodarone.

In one embodiment, the granules are prepared in a dry granulation process.

In one embodiment, these granular formulations comprise a crystalline sugar alcohol that enhances the rate of budiodarone release in a simulated test protocol for assessing drug release in vivo. When incorporated into the formulations described herein, the crystalline sugar alcohol reduces aggregation associated with granular formulations employing spray-dried mannitol, but also results in granular formulations that exceed the release requirements of the simulated test protocol. Moreover, the use of crystalline sugar alcohols increases the dissolution rate of budiodarone during the first 15 minutes and again in the first 30 minutes of the one hour test as compared to the same formulation using spray-dried sugar alcohols. In some embodiments, these formulations are capable of releasing at least about 75% of the active into the fluid within 30 minutes from the start of the test protocol.

Accordingly, in one embodiment, there is provided a granular formulation of a crystalline budiodarone salt which comprises an effective amount of a crystalline budiodarone tartrate salt, microcrystalline cellulose, an effective amount of a crystalline sugar alcohol, one or more lubricants, and a disintegrant or a super disintegrant.

In one embodiment, the crystalline salts employed in such formulations comprise a budiodarone salt selected from a mono-tartrate salt, a mono-fumarate salt, and a mono-citrate salt.

In one embodiment, the granular formulations described herein employ a crystalline budiodarone mono-tartrate salt, which is characterized by the XRD pattern of FIGS. 1A and 1*s* referred to as Form-1.

In one embodiment, these granular formulations further comprise a crystalline sugar alcohol, one or more lubricants, and a disintegrant or super disintegrant.

In one embodiment, the granules described herein comprise a coating to enhance their properties. The granule is sometimes referred to herein as being intra-granular, and the coating as being extra-granular.

In one embodiment, the extra-granular coating comprises a lubricant.

In one embodiment, the crystalline sugar alcohol is intra-granular. In another embodiment, the crystalline sugar alcohol is added as a part of an extra-granular lubricant coating. In yet another embodiment, the crystalline sugar alcohol is both intra-granular and part of the extra-granular lubricant coating.

In one embodiment, the crystalline sugar alcohol as used herein preferably has 5 or 6 carbon atoms and, more preferably, is selected from mannitol, sorbitol, or xylitol.

In one embodiment, the crystalline sugar alcohol is a crystalline mannitol.

In one embodiment, the formulations comprise a microcrystalline cellulose, crystalline mannitol, magnesium stearate, colloidal silica dioxide, and a crosslinked polyvinylpyrrolidone disintegrant.

In one embodiment, the extra-granular coating comprises one or both of a lubricant and a disintegrant, such as crosslinked polyvinylpyrrolidone.

In one embodiment, the crystalline sugar alcohol has a specific surface area of at least 0.5 $m^2/g$ and an average particle size of about 100 μm or less, preferably 50 μm or less.

In one embodiment, the granular formulation is prepared by dry granulation.

In one embodiment, the crystalline sugar alcohol has a specific surface area of about 0.5 $m^2/g$ or higher.

In one embodiment, the granular formulations described herein are incorporated into a capsule.

In some embodiments, the capsule comprises either a plant-based shell or a gelatinous shell.

In one embodiment, the plant-based shell comprises microcrystalline cellulose.

In one embodiment, the granular formulations described herein are incorporated into a tablet.

In one embodiment, the capsule may include small opening(s), e.g., formed by cutting with a laser or the like (i.e., small laser-generated openings), that allow the solution to flow into gastric fluids after the capsule is ingested.

Another embodiment described herein is a method for enhancing the dissolution of budiodarone from a capsule comprising a formulation containing spray-dried mannitol, which method comprises replacing said spray-dried mannitol with crystalline mannitol.

4. BRIEF DESCRIPTION OF THE DRAWINGS

FIG. 1A provides the X-Ray Diffraction (XRD) pattern of crystalline budiodarone tartrate crystallized from isopropanol and water. FIG. 1B provides the X-Ray Diffraction (XRD) pattern of crystalline budiodarone tartrate crystallized from acetonitrile and water. These two XRD patterns are believed to be identical.

Figure 10:
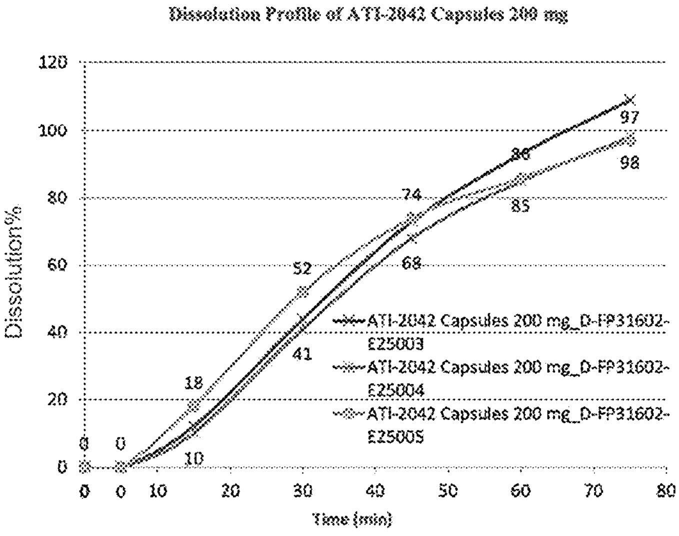

FIG. 10 provides a further evaluation of a hard gelatin capsule versus a microcrystalline hard capsule.

5. DETAILED DESCRIPTION

Disclosed are granular formulations of crystalline budiodarone tartrate having suitable dissolution rates for use in capsules and tablets.

Terminology

The following provides clarity to certain terms and phrases used in this application. It is understood that terms or phrases used herein that are not defined have their accepted chemical or biological meaning.

Unless otherwise clear from context, all percentages set forth herein are expressed as percentage by weight (wt. %) based on the total weight of a composition.

As used herein, the singular forms "a", "an," and "the" are intended to include the plural forms as well, unless the context clearly indicates otherwise.

As used herein, the term "about" when used before a numerical designation, e.g., temperature, time, amount, concentration, and such other, including a range, indicates approximations that may vary by (+) or (−) 10%, 5%, 1%, or any subrange or a sub value therebetween. In some embodiments, the term "about" when used concerning a dose amount means that the dose may vary by +/−5%.

As used herein, the term "comprising" or "comprises" is intended to mean that the compositions and methods include the recited elements but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure.

As used herein, the term "consisting of" shall mean excluding more than trace elements of other ingredients and substantial method steps. Embodiments defined by each of these transition terms are within the scope of this disclosure.

For purposes of claim interpretation in the United States, the term "preferably" should be read out of any sentence and/or paragraph in the main body of the specification.

As used herein, the term "anhydrous", as it refers to crystalline budiodarone salts, means that its crystal structure is substantially free of water except for some adventurous amounts of residual water totaling no more than 0.5 weight percent at 20° C. and preferably less than 0.3 weight percent (wt. %) also at 20° C.

As used herein, the term "granules" refers to granular particles optionally containing an extra-granular coating.

As used herein, the term "minor amount of water" when referring to multi-component solvent systems means that the weight percent of water is no more than 25% relative to the weight of a hydrophilic aprotic or protic (non-water) solvent(s) used in the crystallization solvent. In some embodiments, the weight percent of water in these solvents is no more than 20% or no more than 15% or no more than 10%. In some cases, the weight percent of water used is about 1:15 based on the weight of the non-aqueous solvents. In one embodiment, the hydrophilic aprotic solvent is acetonitrile. Protic solvents include $C_1$-$C_4$ alcohols, including isopropanol. Due to impurities that arise during crystallization, protic solvents are not preferred.

As used herein, the term "agglomeration-resistant" or "aggregation-resistant" means that the degree of agglomeration or aggregation experienced during tableting or filling a capsule is consistent with validated cleaning procedures that are followed consistently so as to comply with Good Manufacturing Practices (GMP). See, for example, a Pharmland publication on the internet at pagmachinery.com/how-should-i-clean-and-maintain-a-capsule-filling-machine-to-meet-gmp-standards/, which provides for a discussion on cleaning techniques, timing, and the like to comply with GMP standards. The degree of agglomeration or aggregation of the formulation that still complies with an intermittent cleaning schedule consistent with GMP is deemed to be an agglomeration-resistant formulation.

As used herein, the term "flowable" means that the degree of agglomeration due to anisotropic characteristics of the crystalline budiodarone salt has been mitigated by the formulation such that the flow of granular particles into a die press of a tableting device or into a capsule is consistent with any deviation in the amount of active drug incorporated into the capsule or tablet is consistent with regulatory standards. For example, if the allowed relative standard deviation of the weight of the active in a capsule is within +/−5% by weight, then a capsule that is to be filled to 200 mg of active drug has regulatory approval if the capsule contains between 190 and 210 mg of the active drug. As such, sophisticated check-weighing systems statistically monitor filled capsules to ensure that they are within a specific weight range. Formulations that fail such requirements are deemed to lack flowability. Similar requirements are mandated for tablets.

As used herein, the term "pharmaceutical disintegrant" or "disintegrant" is based on the US Pharmacopeia definition, which is "an agent added to a tablet or capsule formulation to facilitate the breakup or disintegration of the tablet or capsule into smaller pieces that dissolve more rapidly in the gastrointestinal tract." As is well established in the art, pharmaceutical disintegrants are separated into two categories: disintegrants and super disintegrants, and the term "pharmaceutical disintegrant" covers both categories. The distinction between the two is that super disintegrants facilitate very rapid release of the active in a capsule or a tablet (e.g., less than one hour) while using only 1% to 10% by weight of the super disintegrant, while disintegrants not defined as super disintegrants lack one or both of these properties.

A list of suitable disintegrants is provided in PE Pharma Excipients, <<www.pharmaexcipients.com/disintegrants/>>. Included in the list are "natural disintegrants" such as alginic acid, bentonite, powdered cellulose, guar galactomannan, as well as semi-synthetic disintegrants such as carboxymethylcellulose calcium, carmellose sodium, croscamellose sodium, sodium starch glycolate Type A and B, low-substituted carboxymethylcellulose sodium, and low-substituted hydroxypropyl cellulose. As to synthetic disintegrants, only crospovidone was mentioned. Each of the PE Pharma Excipients lists is incorporated herein by reference in its entirety.

As used herein, the term "super disintegrant" refers to those agents added to a tablet or capsule formulation to facilitate the breakup or disintegration of the tablet or capsule into smaller pieces that dissolve more rapidly in the gastrointestinal tract as compared to disintegrants in general. A list of super disintegrants is available at, for example, <<www.researchgate.net/figure/List-of-Super-Disintegrants_tbl1_259466262>>, which is provided in Table 1 below.

TABLE 1

| Super-disintegrants | Example | Mechanism of action | Special comment |
|---|---|---|---|
| Crosscarmellose ® Ac-Di-Sol ® Nymce ZSX ® Primellose ® Solutab ® Vivasol ®L-HPC | Crosslinked cellulose | Swells 4-8 folds in <10 seconds. Swelling and wicking both. | Swells in two dimensions. Direct compression or granulation Starch-free |
| Super-disintegrants | Example | Mechanism of action | Special comment |
| Crosspovidone Crosspovidon M ® Kollidon ® Polyplasdone ® | Crosslinked PVP | Swells very little and returns to its original size after compression but acts by capillary action | Water insoluble and spongy in nature, so get porous tablet |
| Sodium starch glycolate Explotab ® Primogel ® | Crosslinked starch | Swells 7-12 folds in <30 seconds | Swells in three dimensions and high level serves as a sustained release matrix |
| Alginic acid NF Satialgine ® | Crosslinked alginic acid | Rapid swelling in aqueous medium or wicking action | Promote disintegration in both dry and wet granulation |
| Soy polysaccharides Emcosoy ® | Natural super disintegrant | Does not contain any starch or sugar. Used in nutritional products | |
| Calcium silicate | | Wicking action | Highly porous, Optimum concentration is between 20-40% |

In general, super disintegrants are used, among which are synthetic disintegrants, crosslinked polyvinylpyrrolidone disintegrants, and, in particular, Crospovidone Kollidon CL, available from BASF, Florham Park, New Jersey, USA.

As used herein, the term "thermally stable" means that the crystalline salts of budiodarone do not melt, decompose, sublime, undergo a phase transition (e.g., crystalline to amorphous) or otherwise fails to retain its crystal structure, even when exposed to a temperature of up to 50° C. and/or a pressure of up to 20,000 pounds per square inch (psi). The term "thermally stable" is interchangeable with "compression stable."

The term "compressible" means that the granules of anhydrous crystalline budiodarone salts can be compressed when mixed with excipients to form a tablet or a capsule.

The term "hydrophilic aprotic solvent" refers to a class of solvents exhibiting hydrophilic properties, but which lack exchangeable protons ($H^+$), such as found in protic solvents containing carboxylic, hydroxy, and/or amino groups. Examples of such hydrophilic aprotic solvents include tetrahydrofuran, acetonitrile, dimethylsulfoxide, acetone, and N,N-dimethylformamide. In some embodiments, the hydrophilic aprotic solvent is selected from acetonitrile and tetrahydrofuran.

As used herein, the term "residual hydrophilic aprotic solvent" refers to the amount of such solvent retained in the crystal structure after crystallization or recrystallization and drying. In one embodiment, such residual hydrophilic aprotic solvent is less than about 1,000 ppm in the crystalline budiodarone tartrate. In another embodiment, the residual hydrophilic aprotic solvent is less than about 500 ppm in the crystalline budiodarone tartrate. In still another embodiment, the residual hydrophilic aprotic solvent is less than about 400 ppm or 300 ppm in the crystalline budiodarone tartrate.

As used herein, the term "$C_1$-$C_4$ alcohol" refers to methanol, ethanol, isopropanol, n-propanol, n-butanol, iso-butanol, sec-butanol, and t-butanol. Because of its low boiling point, methanol is not a preferred alcohol.

As used herein, the terms "AF", "AFib", and "atrial fibrillation" refer to all variants of atrial fibrillation except permanent AFib. The methods of treatment disclosed are not contemplated for treating a patient with permanent AF. Such AF variants include but are not limited to paroxysmal AF, persistent AF, and incipient AF, as well as paroxysmal AF and persistent AF with low $CHA_2DS_2$-VASc scores (2 or less) and high $CHA_2DS_2$-VASc scores (3 or higher).

As used herein, "AF duration" is the length of time of a single AF episode. As used herein, the term "extended duration of AFib" relates to the length of time an episode of AF lasts in a patient. This length relates to the risk of stroke and/or heart failure. The longer the length of time a patient is in AFib, the higher the risk becomes. So, in one embodiment, an extended duration of AFib includes any AFib episode lasting over at least about 30 minutes, or at least about 1 hour, or at least 5 hours, provided that the patient is not diagnosed as having permanent AFib. The "number" of episodes is the number of long-duration AF episodes having a duration greater than 1 hour or greater than 5 hours. The term "duration" means the length of the AF episodes. AF Burden (AFB) is the percentage of time in any set period of time (e.g., 7 days, 14 days, or 28 days) spent in AF. If the AFB is high, it generally contains long-duration AF (e.g., greater than 1 hr or greater than 5 hrs). The number can also, or alternatively, refer to a number of AF episodes of greater than 6 minutes.

The presence of AF, especially with frequent long episodes of AF>5 hours, significantly shortens the time in diastole for passive filling of the left ventricle. When combined with the loss of atrial contraction in AF, which eliminates the active diastolic filling of the left ventricle, cardiac output drops. Reduced time in diastole and elimination or reduction in active diastolic filling of the left ventricle are critical to maintaining sufficient cardiac output to perfuse the body with blood. In patients with a cardiomyopathy and in normal sinus rhythm (NSR) and with New York Heart Association (NYHA) stage I and II HF, the cardiac output is barely adequate to perfuse the body. When such a patient then develops new-onset AF, even a small amount, such as PAF with low AFB, or a lot, such as persistent AF with 100% AFB, the ventricular filling during diastole is further compromised such that the cardiac output drops dramatically, and perfusion of the body is now clearly inadequate to sustain life and hence, the hazards ratio for mortality increases to 4.99 and life expectancy is significantly shortened, often to a matter of months. The addition of AF throws the previously compensated HF patient into NYHA Stage III or Stage IV.

As used herein, the terms "paroxysmal AFib" and "PAF" refer to sporadic and intermittent episodes of AFib that last no more than 7 days before resolving back into sinus rhythm. Typically, but not necessarily, patients with de minimis AFib (or incipient AFib) are not characterized as having paroxysmal AFib except for patients with HF as a comorbidity and incipient AFib, who are treated as having paroxysmal AFib.

As used herein, the term "persistent AFib" refers to sporadic and intermittent episodes of AFib that last more than 7 days and may not resolve back into sinus rhythm without medical intervention (e.g., cardioversion).

The phrases "therapeutically effective amount", "effective amount", and "pharmaceutically effective amount" are used interchangeably and mean a nontoxic but sufficient amount of budiodarone or a pharmaceutically acceptable salt of budiodarone, or a pharmaceutical composition comprising the same, to provide the desired biological result, and/or to an amount sufficient to carry out a specifically stated purpose. A therapeutically effective amount may require the administration of multiple capsules or tablets, each of which comprises a sub-dosage amount of budiodarone, but which together form a therapeutically effective dosage. In some aspects, a therapeutically effective amount is sufficient to alter a condition or symptom in the patient. The condition or symptom can include:

(i) fewer AF episodes of AF lasting more than 5 hours;
(ii) decreased pulmonary congestion as determined by chest X-ray;
(iii) a decreased AF burden over a set period of time;
(iv) fewer AF episodes over a set period of time;
(v) fewer AF episodes over a set period of time lasting more than 1 hour;
(vi) an averaged increase in exercise tolerance in HFrEF over a set period of time after administration of the budiodarone or its pharmaceutically acceptable salt as compared to before administration of the budiodarone or its pharmaceutically acceptable salt to the patient;
(vii) an averaged increase in exercise tolerance in HFpEF over a set period of time after administration of the budiodarone or its pharmaceutically acceptable salt as compared to before administration of the budiodarone or its pharmaceutically acceptable salt to the patient;
(viii) an averaged decreased in shortness of breath at rest in HFpEF and HFrEF over a set period of time after administration of budiodarone or its pharmaceutically acceptable salt as compared to before administration of the budiodarone or its pharmaceutically acceptable salt to the patient;
(ix) less patient fatigue (improved stamina) than before budiodarone or its pharmaceutically acceptable salt was administered to the patient;
(x) reduced patient dyspnea than before budiodarone or its pharmaceutically acceptable salt was administered to the patient;
(xi) less swelling (edema) in the arms, legs, hands, abdomen (ascites), and/or ankles of the patient than before budiodarone or its pharmaceutically acceptable salt was administered to the patient; and
(xii) less coughing by the patient over a set period than before budiodarone or its pharmaceutically acceptable salt was administered to the patient.

It is understood that for some of the listed conditions, patient monitoring is necessary to demonstrate and track patient improvement; for these conditions, the monitoring can be continuous or semicontinuous. Preferably, the monitoring should be continuous and should use a wearable monitor. For other symptoms, such as shortness of breath, improved stamina, dyspnea, edema, less coughing, and improvements in exercise tolerance, continuous monitoring would not be necessary. See, e.g., U.S. Pat. Nos. 12,257,228, 12,115,373, 11,975,202, 11,839,768, and 11,759,640, each of which is incorporated herein by reference in its entirety.

The phrases "a patient in need of treatment" and "a subject in need of treatment," according to the methods described herein, may be a patient diagnosed with a heart arrhythmia that is amenable to treatment with budiodarone. Examples of such heart arrhythmias include paroxysmal and persistent AFib, paroxysmal and persistent AFib coupled with heart failure.

The term "pharmaceutically acceptable salts" as used herein is meant to include salts of budiodarone that form crystalline structures. A preferred crystalline structure for budiodarone is polymorph Type-1.

Included in the term "crystalline" are semi-crystalline salts such as citrate salts, hydrochloride salts, and fumarate salts, wherein at least 60% of a given particle is crystalline, with the remainder evidencing portions that are amorphous. To the extent that a semi-crystalline salt contains particles that are entirely crystalline, then, as first shown by Louis Pasteur, these crystals can be separated from other partially crystalline and non-crystalline (amorphous) particles by visual observation, optionally using magnification tools. Further, when the crystal size is larger than the amorphous particles, the use of a screen should separate those particles having higher rates of crystallinity. In the case of citrate and fumarate salts of budiodarone, the crystalline portions of these structures provide the same or similar XRD patterns as compared to the crystalline budiodarone tartrate Form-1. Such evidence suggests the same or similar short needle-like crystal structures as Form-1 of budiodarone tartrate. Still further, since the amorphous portion is still the same budiodarone salt, it is contemplated that any or all of the amorphous product could be used herein. If, for example, separation of the crystalline portions from the amorphous portions retains a small amount (less than 20% or less than 10%) of amorphous budiodarone salt, then that small amount is still budiodarone tartrate, which can be incorporated into the granules as described herein.

As used herein, the term “budiodarone” refers to the free base compound, which has the formula:

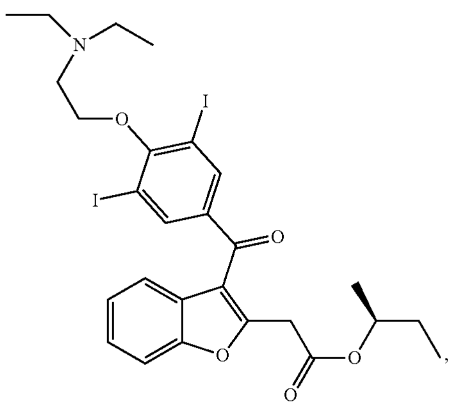 [SMILES: CC[C@H](C)OC(=O)Cc1oc2ccccc2c1C(=O)c1cc(I)c(OCCN(CC)CC)c(I)c1]

and whose IUPAC nomenclature is(S)-sec-butyl 2-(3-(4-(2-(diethylamino) ethoxy)-3,5-diiodobenzoyl)benzofuran-2-yl) acetate.

As used herein, the term “budiodarone tartrate” refers to the tartrate salt of budiodarone with the formula:

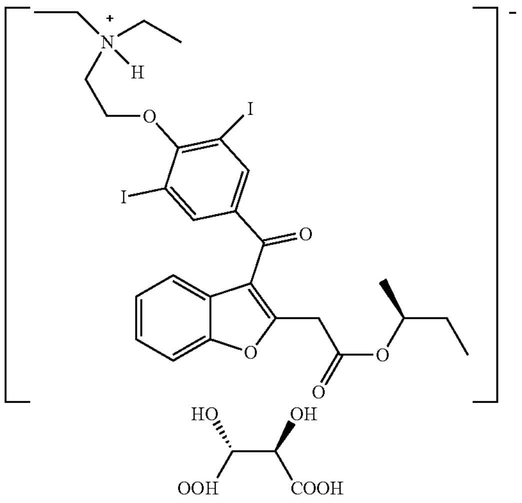

Likewise, the citrate and fumarate salts of budiodarone have the formulas:

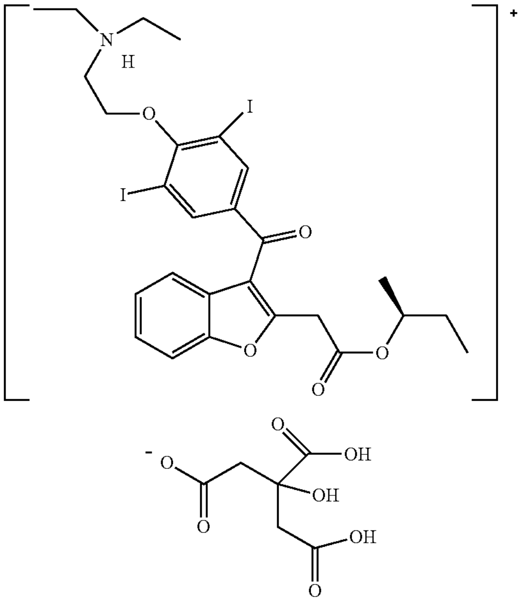

citrate

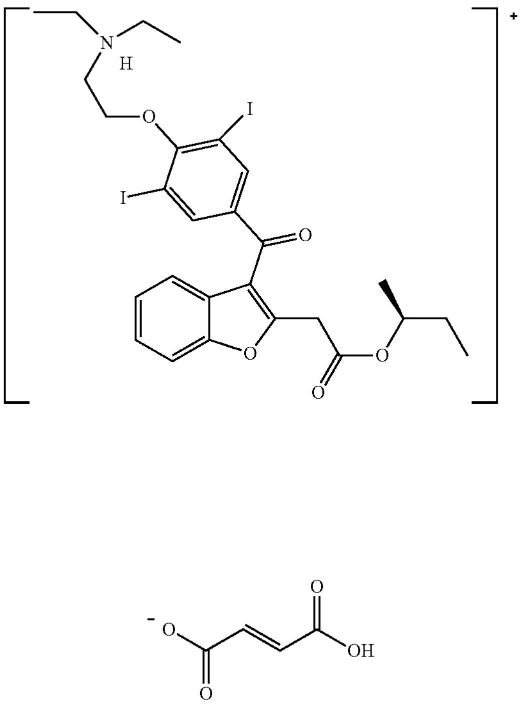

fumarate

TABLETS and Capsules

Crystalline budiodarone tartrate ("CBT") is produced by crystallization of the amorphous salt in a co-solvent mixture containing isopropanol:water as disclosed in U.S. Pat. No. 9,954,912 (the '912 patent). CBT is disclosed in the art as treating paroxysmal and persistent AFib by eliminating long episodes of AFib, thereby reducing the risk of stroke and heart failure due to AFib. See, e.g., U.S. Pat. Nos. 12,257,228, 12,115,373, 11,975,202, 11,839,768, and 11,759,640, which are incorporated herein in their entirety. In some embodiments, CBT is orally administered, preferably either as a tablet or a capsule.

A. Crystallization

As per the '912 patent, crystallization of budiodarone tartrate was done in isopropanol and water, and produced needle-like crystals, which are undesirable. Attempts to prepare other crystalline polymorphs of budiodarone tartrate, as well as other budiodarone salts, were conducted. Budiodarone crystallization attempts were conducted on a library of different salts for water solubility, thermal stability, and other properties for drug ability.

Five (5) salts were considered for further analysis, as the other salts were deemed unacceptable. These five budiodarone salts include the mono-citrate salt, the mono-fumarate salt, the mucate salt, and the hemi-salt of aspartate. Each of these salts was partially crystalline under the conditions used. The citrate and fumarate salts had some beneficial properties, whereas the remaining three were deemed to be unacceptable. As to the citrate and fumarate salts, the budiodarone citrate salt has excellent water solubility, whereas the budiodarone fumarate salt has a water solubility of 0.35 mg/mL at 25° C. in unbuffered water. The XRD of both the citrate and fumarate salt forms of budiodarone appeared to be the same as Form 1 of budiodarone tartrate, but minor peaks (possibly impurities) were not evaluated. Surprisingly, each of the tartrate, citrate, and fumarate salts was a mono-salt having two or three carboxyl groups. Given their relative sizes and multiple carboxyl groups, only one of which was the carboxylate acting as the counter ion, it would seem that these similarities could explain why the XRD patterns for each are the same or similar.

In addition, further evaluation of crystallization solvents could be undertaken to obtain crystalline budiodarone citrate and crystalline budiodarone fumarate instead of the semi-crystalline material initially found. Alternatively, the methods described above for isolating crystalline samples could be employed.

B. Crystalline Impurities

The proposed dosing schedule for budiodarone tartrate to treat paroxysmal and persistent AFib includes doses that range from 200 to 800 mg per day twice a day (including 100 mg interval dosages in between 200 mg and 800 mg such as 300 mg, 500 mg, etc., but, in some cases, the dose may be as low as 100 mg twice a day or as high as about 1.1 g as a bolus dose). As such, a high aggregate amount of budiodarone tartrate is dosed to the patient every day. This, in turn, means that even small amounts of impurities remaining in the crystalline product can pose a significant problem. Such a problem can be exacerbated if one of the metabolites of one or more of these impurities is slowly eliminated from the body. In such cases, the amount of such metabolites can accumulate in the body over time and pose a significant health risk.

When evaluated, the impurity profile for crystalline budiodarone tartrate prepared as per the '912 patent using isopropanol/water co-solvent as the crystallization solvent was deemed to be unacceptable, as multiple contaminants were found to be in excess of 0.10 weight percent, and one impurity was in excess of 0.15 weight percent. Moreover, the accumulated amount of the three impurities was in excess of 1 mg per day when dosed at least at 400 mg BID.

Some of these impurities were difficult to characterize. However, once characterized, the believed source of these impurities was identified. Based on the identification of three of these impurities coupled with knowing the temperature and time required to solubilize amorphous budiodarone tartrate in the isopropanol water crystallization co-solvent as per the '912 patent (the "'912 sample"), it was hypothesized that the extended heating required to solubilize budiodarone tartrate in the co-solvent allowed for budiodarone tartrate to undergo unintended reactions possibly assisted by or incorporating the isopropanol as a reagent in these reactions. For example, Impurities 1, 2, and 5 are identified in Table 2 below. As to Impurity 1, it is believed to be attributed to decarboxylation arising from the extended period of heating required to effect solubilization. However, when recrystallization of the '912 sample was conducted in acetonitrile: water, this impurity was not found. This suggested that this impurity was removed from the '912 sample during recrystallization and that the extent of time and temperature required for this recrystallization did not generate any of this impurity. One possible reason for this result is that the isopropanol used in the '912 sample participated in the decarboxylation reaction during crystallization, whereas acetonitrile does not.

As to Impurity 2, this is attributed to transesterification, whereby isopropanol replaces the butyl portion of the ester. As above, transesterification is believed to be facilitated by the high heat and extended duration required to solubilize the amorphous budiodarone tartrate. As with Impurity 1, Impurity 2 was not detected after recrystallization of the '912 sample using acetonitrile and water.

Impurities 3 and 4 are and remain unknown as their weight percent was within acceptable ranges.

Impurity 5 is believed to be the product of an elimination reaction, which results in the formation of a 3,5-diiodo-4-phenol group, which is believed to be assisted by intramolecular or intermolecular interaction of the amino group of the N,N-diethylaminoethyl group. While not shown, once the 3,5-diiodo-4-phenol is formed, it is believed that the release of iodine will rapidly occur in vivo, resulting in the formation of the indole-carbonyl-phenol. As shown below, one possible degradation pathway could result in the formation of:

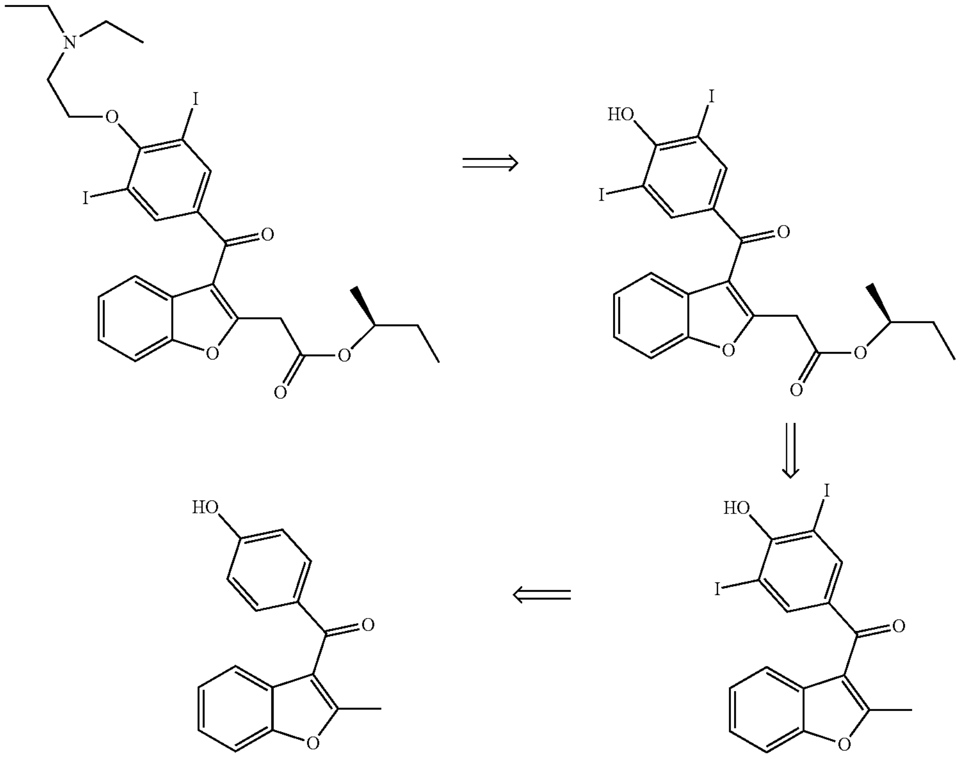

While the final impurity shown has not yet been identified in the crystalline product, it is contemplated that such might be a metabolite that would form in vivo as a result of the elimination of the iodo groups from the decarboxylated product.

Table 2 below summarizes these impurities.

TABLE 2

| | Structure | Note | Form 1 |
|---|---|---|---|
| Impurity 1<br>Decarboxylate<br>Rt = 14.272 min<br>MW = 602.98 | 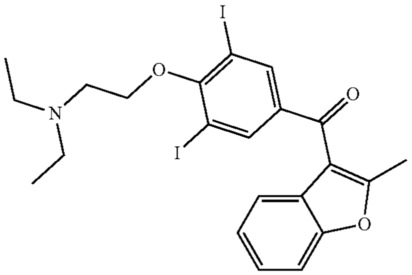 [SMILES: CCN(CC)CCOc1c(I)cc(C(=O)c2c(C)oc3ccccc23)cc1I] | Formed by heating and decarboxylating | 0.120 weight % |
| Impurity 2<br>IPA-analogue<br>Rt = 15.418 min<br>MW = 690.00 | 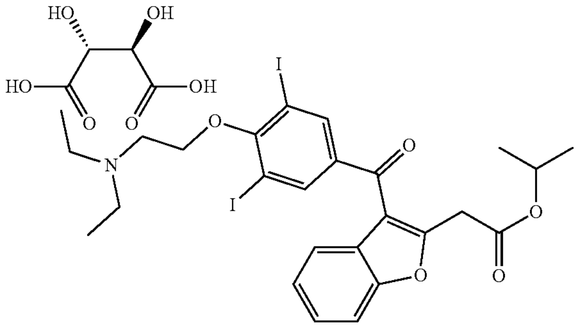 | Transesterification | 0.093 weight % |

TABLE 2-continued

| | Structure | Note | Form 1 |
|---|---|---|---|
| Impurity 3<br>Unknown 1<br>Rt = 16.134 min | N/A | Unknown impurity | 0.036 weight % |
| Impurity 4<br>Unknown 2<br>Rt = 17.845 min | N/A | Unknown impurity | 0.025 weight % |
| Impurity 5<br>EL-7<br>Rt = 35.056 min<br>MW = 604.17 | 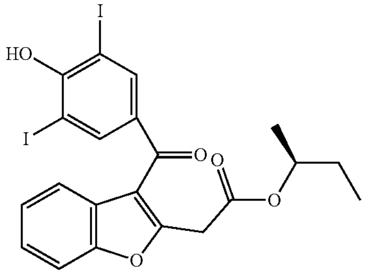 | Elimination reaction | 0.167 weight % |
| Total | | | 0.441 weight % |

After ascertaining that isopropanol was the likely source of a number of impurities in the crystalline budiodarone tartrate composition, non-aprotic solvents were considered as an alternative crystallization solvent, optionally using a minor amount of water. However, it remained uncertain as to what crystallization solvent would provide for a crystalline product while not introducing other impurities, especially at a higher level than that of isopropanol. Moreover, based on the fact that the citrate, hydrochloride, and fumarate salts produced a semi-crystalline composition, it was uncertain whether the tartrate salt would also produce a semi-crystalline composition using an aprotic crystallization solvent (or co-solvent with water) or if a crystalline form was generated, whether it would have an acceptable impurity profile.

C. Resolution of the Impurities Concern

As disclosed in U.S. Provisional Patent Application Ser. No. 63/804,515, CBT obtained from the isopropanol:water co-solvent was recrystallized using acetonitrile:water co-solvent, which, based on apparently the same XRDs, also provided for Form 1 of crystalline budiodarone tartrate while eliminating most of the impurities present in that composition. Table 3 below provides an average of three (3) separate Certificates of Analysis of individual batches of recrystallized CBT.

TABLE 3

| CERTIFICATE OF ANALYSIS (average of 3 runs) | | |
|---|---|---|
| Test | Specification | Result |
| Appearance | White to yellow to beige | White |
| Identity by FTIR | Spectrum conforms to the reference | Conforms |
| Identity by HPLC by RT | Retention time of the main peak conforms to the reference standard +/- 5% | Conforms |
| Heavy metals as Pb | NMT 20 ppm | <20 ppm |
| Water content (KF) | NMT 2.0% | 0.367% (3,4,4) |
| Residue on Ignition | NMT 0.30% | 0% |
| Purity by HPLC | NMT 97% | 99.9% |
| Assay by HPLC (free base) | 79.1-84.9 (w/w vs. standard) | 81.67 (81.2, 81.8, 82.0) |
| Total Impurities (by HPLC) | NMT 3.0 weight percent | 0.06 weight percent |
| Individual Impurity | NMT 0.1 weight percent | 0.06 weight percent |
| Chiral purity | NLT 97.0% | 99.9% |
| | Residual solvents | |
| Methanol | NMT 3000 ppm | 23 ppm (24, 27, 18) |
| Isopropyl alcohol | NMT 5000 ppm | 4.7 ppm (6, 5, 3) |
| Acetonitrile | NMT 410 ppm | 33.3 ppm (34, 33, 33) |
| Dichloromethane | NMT 600 ppm | ND |
| 2-butanol | NMT 5000 ppm | 10.3 (11, 13, 10) |
| Ethyl Acetate | NMT 5000 ppm | ND |
| Tetrahydrofuran | NMT 720 ppm | 1 ppm |
| Toluene | NMT 890 ppm | 2 ppm |

In comparing the number and extent of impurities generated by the isopropanol:water crystallization co-solvent to that of the acetonitrile:water co-solvent, there is a significant reduction both in the number of impurities and in the aggregate weight percent of impurities when using the acetonitrile:water as the crystallization solvent. Specifically, crystallization with isopropanol water co-solvent produced the five (5) impurities having an aggregate weight percent of 0.44 weight percent (wt. %), whereas crystallization using an acetonitrile:water ratio of about 15:1 as the solvent produced a single impurity at 0.06 weight percent.

As described above, isopropanol is considered to be the source of at least three (3) of the five (5) impurities in samples crystallized using isopropanol and water coupled with heating. As such, if recrystallization was conducted using the same isopropanol water co-solvent, it is contemplated that additional impurities would form while retaining those from the initial crystallization. Such would result in increasing the amounts of each of these impurities during recrystallization rather than removing them.

D. Agglomeration

Initial attempts to use crystalline budiodarone tartrate Form-1 in a capsule or tablet preparation resulted in the formation of random agglomerates, which prevented the formation of a composition with uniform density. Such uniform density in the composition is necessary to ensure that individual capsules and tablets have equivalent amounts of the active drug ingredient in each capsule filled or tablet made. Unfortunately, agglomeration causes an inconsistent delivery of budiodarone tartrate into unit dose compositions, resulting in variations that fall outside of accepted dosage uniformity, such as those set forth by the US Pharmacopeia, the Japanese Pharmacopeia, and the European Pharmacopeia, making such unit dose compositions unusable. For example, as shown in Comparative Example D, an attempt to fill capsules with a formulation evidencing agglomeration provided a success rate of 19%.

To address the agglomeration issue, high-resolution pictures of crystalline budiodarone tartrate were obtained. These high-resolution pictures indicated that the budiodarone tartrate crystals were short, needle-like structures due to anisotropic crystal growth.

Such needle-like crystals have been reported as causing a number of formulation issues, including the formation of agglomerates that are tacky and stick to the walls of the equipment used to deliver the pharmaceutical composition into the capsule or tablet.

One approach to alleviate agglomeration involved modifying the crystal shape from needle-like crystals to cubes or spheres. See H. Zhang et al., "Prevention of Crystal Agglomeration: Mechanisms, Factors, and Impact of Additives," *Crystals* 2024, 14, 676. However, this approach fails to account for the importance of crystal anisotropy on pharmacological properties. E. Hadjittofis et al., "Influences of Crystal Anisotropy in Pharmaceutical Process Development," *Pharm. Res.* (2018) 35:100. Anisotropic particles of a crystal structure found at the boundaries may align in a perpendicular fashion to the rest of the crystal. See M. Trebbin et al., "Anisotropic particles align perpendicular to the flow direction in narrow microchannels," *PNAS* 10 (17): 6706-6711, 2013. Modifying the structure of budiodarone tartrate crystals has proven difficult at best (see, e.g., the Crystallization section supra) and, even if successful, could encounter unstable crystal structures, unacceptable crystallization impurities, as well as an inability to reproducibly form tablets or fill into capsules.

There are numerous reports in the literature that such crystal structures should be avoided in favor of cubic or spherical crystal structures. However, as above, there are currently no examples of stable, crystalline budiodarone salts other than those herein provided, which form or are believed to form needle-like crystalline structures.

In the absence of alternative crystal structures, the art provides a number of techniques to address formulation issues, including the use of glidants and lubricants.

Formulations

A. Based on Talc as a Glidant

Figure 3:
FIG. 3 illustrates the agglomeration of a composition comprising the crystalline budiodarone tartrate Form 1, microcrystalline cellulose, talc, and lubricants, which coat the bin of the blender.

To obviate the impact of crystal anisotropic properties, formulations comprising microcrystalline cellulose, a glidant (talc), and one or more lubricants were prepared. As provided in detail in Comparative Example A below and as shown in FIG. 3, the resulting composition remained tacky, as evidenced by the material sticking on the inner surface of the bin that was generated during the blending process. This agglomerate renders these formulations unsuitable for use in devices used for tablet and capsule manufacturing due to their stickiness or tackiness, which causes them to adhere to the equipment. As is apparent, any material sticking to the equipment and not delivered into the capsule or combined into a tablet compromises the amount of active contained therein, which, of course, is unacceptable.

Figure 4:
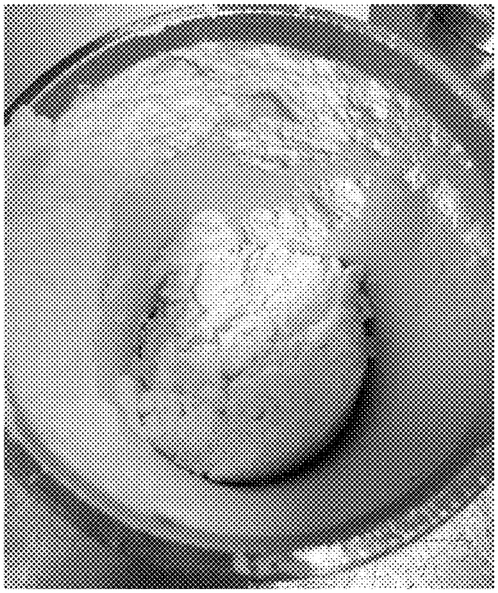
FIG. 4 illustrates that agglomeration was not eliminated despite the further addition of hydroxypropyl cellulose to the formulation.
Figure 5:
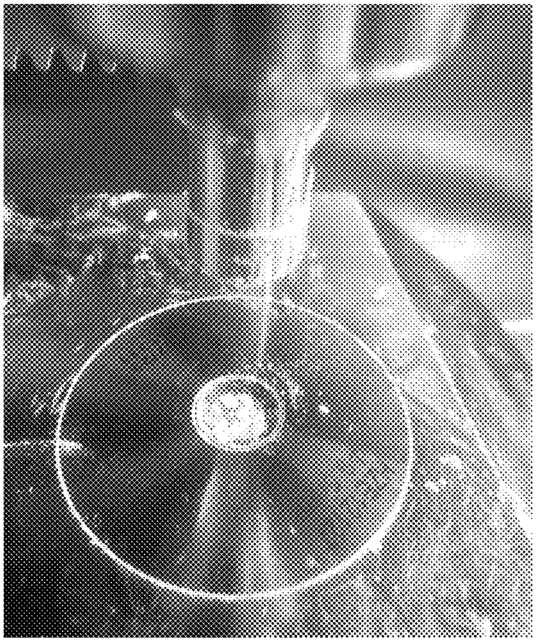
FIG. 5 illustrates that the agglomeration resulted in the sticking of the composition, which was observed on the die punch after about 8 times of compression.

While still using talc and microcrystalline cellulose, hydroxypropyl cellulose was included in the formulation to reduce or eliminate the tackiness of the composition. As per Comparative Example B below, the resulting composition remained tacky and stuck to the inner surface of the bin during blending. FIG. 4 illustrates the level of tackiness of the composition. Attempts to use this formulation in creating tablets required manual die filling due to the poor flowability of the powder blend. Regardless, serious material sticking was observed on the tablet punch after about 8 times of compression, as shown in FIG. 5.

B. Granule Formulations Free of Talc

Based on these results, three new formulations were tried to prepare granules using a dry granulation process, which were free of talc. The granules contained:

- crystalline budiodarone tartrate,
- microcrystalline cellulose,
- intragranular mannitol 100SD (only in formulation 4),
- extra-granular mannitol 100 SD (only in formulation 5)
- intragranular Crospovidone Kollidon CL (CK CL),
- extragranular Crospovidone Kollidon CL
- CDO (colloidal silica dioxide),
- Intragranular magnesium stearate, and
- extra-granular magnesium stearate (mixed as per Example 1).

The specifics for these three formulations are provided in Table 4 as follows:

TABLE 4

| | Formulation 3 | Formulation 4 | Formulation 5 |
|---|---|---|---|
| CBT Form-1 | 52.63% | 52.63% | 52.63% |
| MCC | 26.91% | 26.91% | 26.91% |
| IG Mannitol 100SD | 13.46% 0 | 13.46% | 0 |
| EG Mannitol 100SD | | 0 | 13.46% |
| CDO | 1.00% | 1.00% | 1.00% |
| Int. Mg Stearate | 0.50% | 0.50% | 0.50% |
| Ex. Mg Stearate | 0.50% | 0.50% | 0.50% |
| Int. CKL | 2.50% | 3.50% | 4.50% |
| Ex. CKL | 2.50% | 3.50% | 4.50% |
| Total | 100% | 100% | 100% |

The use of mannitol in formulations in capsules and tablets is known as is the fact that spray-dried mannitol is deemed better suited for use in capsule and tablet formulations. See, <<sigmaaldrich.com/US/en/technical-documents/technical-article/pharmaceutical-and-biopharmaceutical-manufacturing/solid-formulation-strategies/mannitol-in-roll-compaction?srsltid=

AfmBOopOdfltvzEeU_wbUFmnJXjyQ-98gN3CCKz6AAq_EX7arOQiuTP->>. Nevertheless, formulations 3, 4, and 5 retained some but acceptable levels of tackiness.

In addition, the US Food & Drug Administration requires that capsule and tablet formulations must be tested in a standardized dissolution test, which requires that the formulation being evaluated must provide for at least 80% release of the active drug into a simulated gastric fluid within one hour after initiation of the test. A description of this test and conditions used can be found at <<en.wikipedia.org/wiki/Dissolution_testing #: ~:text=The % 20general %20procedure %20for %20a,st il1% 20fails %20the %20Q %20parameter>>, which is incorporated by reference in its entirety. In this case, the test used the well-known USP apparatus 2 (paddles) (see the USP at page <711> for details on USP apparatus 2), a dissolution volume of 900 mL, and a dissolution medium comprising 0.3% Tween 80®, maintained at pH 4.5 with an acetate buffer.

During the dissolution test, some material sticking was observed on the sinkers before 30 minutes, further evidencing retained tackiness, etc. While these results demonstrate that the formulation successfully passed the test requirement at 1 hour (formulation 3=86% released and both formulations 4 and 5=85% released), such was deemed to be marginally successful.

In view of the tackiness remaining, the marginally acceptable release rates at 1 hour, new formulations (Formulations 6, 7, and 8) were prepared, whereby the spray-dried (SD) mannitol 100SD was replaced by crystalline mannitol 50C, which is a crystalline form of mannitol having an average particle size of about 50 microns (μm).

In these formulations, mannitol 50C was used only as an intra-granular component, and the amount of intra-granular and extra-granular CKL started at 2.5 weight percent in Formulation 6, which was increased to 3.5 weight % in Formulation 7 and then to 4.5 weight percent in Formulation 8, as shown in Table 5 above. The formulations in Table 5 are set forth as weight percentages.

Figure 7:
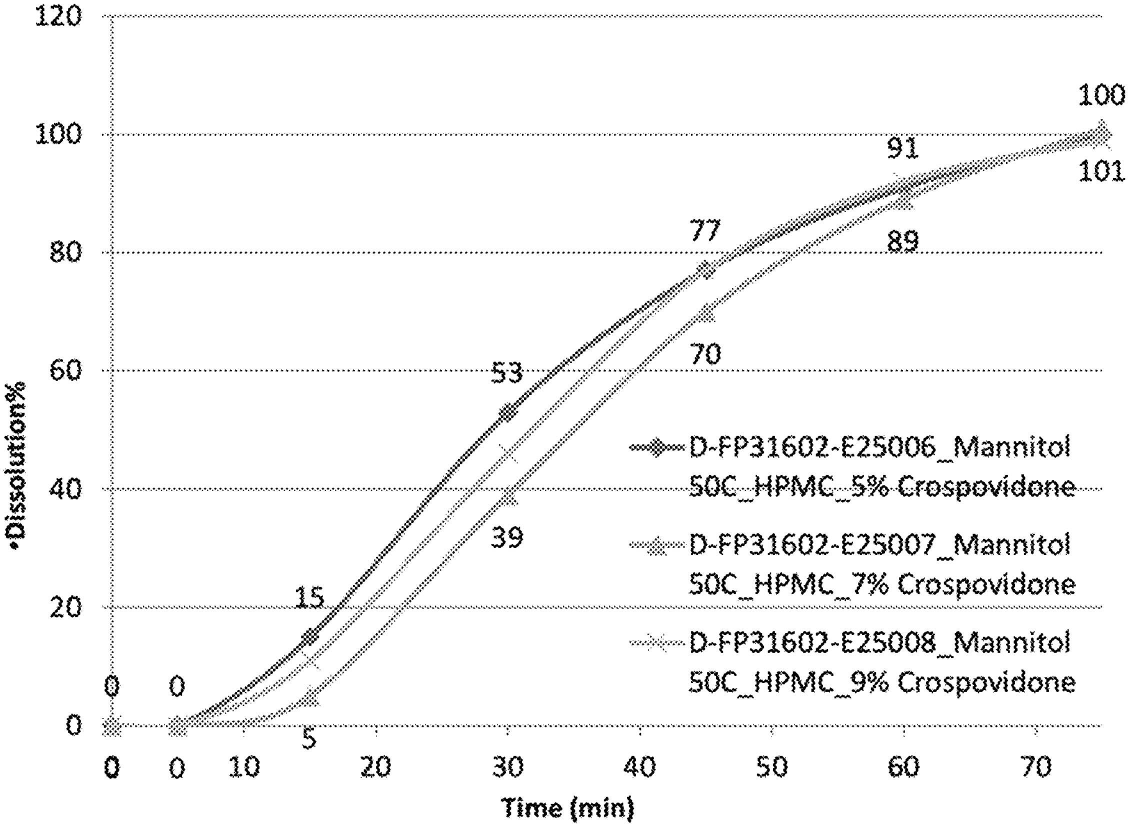

The results of the standardized dissolution test are provided in FIG. 7. Notably, during the first 30 minutes, the addition of crospovidone in excess of 5% appears counterproductive to enhancing the release rate of budiodarone from the formulation, with the lowest concentration of 5% or less yielding the best results. Without being limited to any theory, capsule disintegration provided by crosprovidine is maxed out at 5% and higher concentrations are unneeded and apparently counterproductive.

Figure 6:
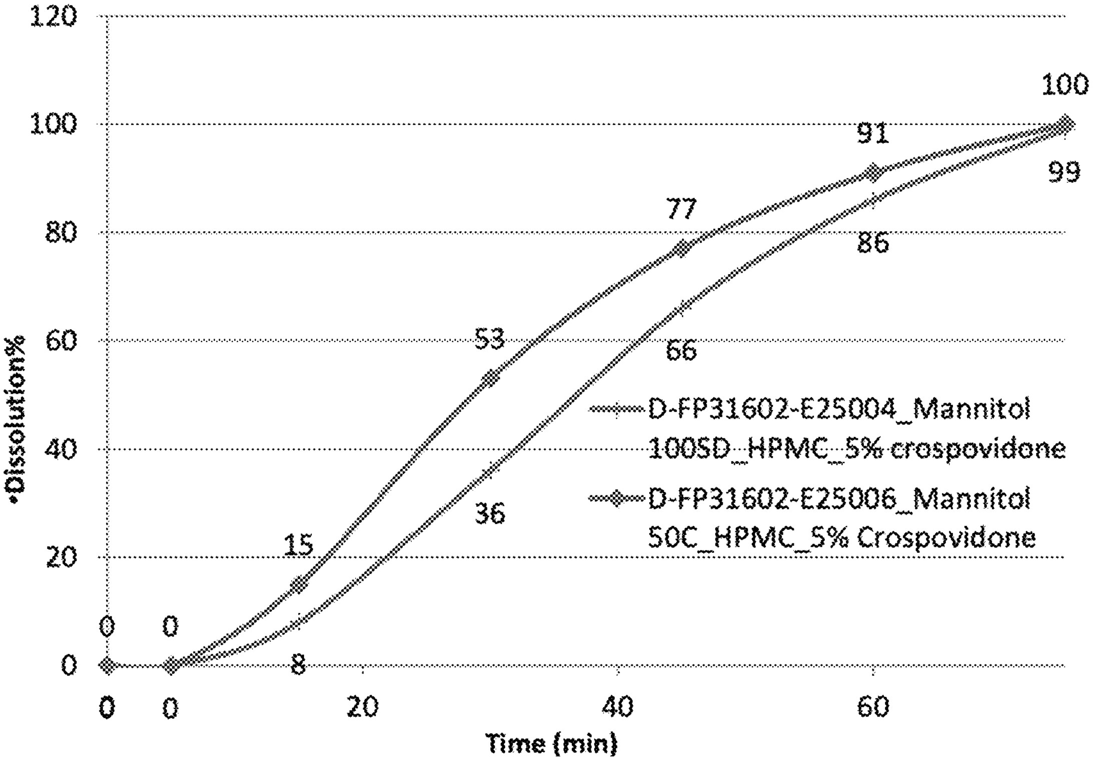
FIGS. 6 and 7 illustrate the release rates of budiodarone from a variety of formulations into simulated gastric fluid.

Surprisingly, a comparison of the dissolution results at the same concentration of crospovidone using either mannitol 100SD or crystalline mannitol 50C shows a surprising result in FIG. 6, where the mannitol 50C provides for almost a 50% increase in dissolution of budiodarone from the capsules using 5% crospovidone compared to the same formulation using spray-dried mannitol 100SD. This differential is also manifested in FIG. 8, where a gelatin capsule replaced a microcrystalline cellulose capsule. Again, the relative almost doubling of the amount of dissolved budiodarone is evident between the formulation using crystalline mannitol 50C and spray-dried mannitol 100SD. In addition to being unexpected, the use of crystalline mannitol for use in the granular formulations has been associated with lengthening the time for dissolution, not shortening it, relative to spray-dried mannitol.

Still further, other crystalline sugar alcohols are deemed suitable in Formulations 6, 7, and 8 in place of crystalline mannitol. It is further contemplated that these crystalline sugar alcohols, having an average particle size of about 100 μm or less; or about 75 μm or less; or about 50 μm or less, are suitable herein. In some embodiments, each of these sugar alcohols can be further defined as having a specific surface area of at least 0.5 $m^2/g$ coupled with an average particle size of 100 μm or less; or 75 μm or less; or 50 μm or less. In the context of particle size, Dv(90) indicates the size at which 90% of the particles in a sample are smaller than that size; Dv(10) indicates the size below which 10% of particles are found; and Dv(50) indicates the size below which 50% of particles are found. For example, the mannitol 100 SD used has a Dv(10) of 20 μm, a Dv(50) of 100 μm, and a Dv(90) of 185 μm.

Granulation was performed as described in Example 2, which first formed the granules, followed by placing a granular coating over the granules. The resulting granules were then assessed for stability under heat and pressure, and were stable against heating to about 50° C. and were also stable against a pressure of about 10 tons for at least about 5 seconds and preferably at least about 10 seconds.

C. Dissolution

As above, the standard dissolution for tablets and capsules dictates that at least 80% of the active drug (in this case, budiodarone) must be released into simulated gastric fluid in a standardized test within 60 minutes. The capsules containing formulation 4 were tested as required and showed that about 86% of budiodarone was released from the capsule within 1 hour, which means each of these formulations was acceptable. However, even though acceptable, the release rate during the first 30 minutes should be increased to well above the 36% of the active drug that was released. See FIG. 6 for the dissolution rate of formulation 4. Note that this means that the majority of the active compound is back-loaded in dissolution into the final 30 minutes of the 1-hour test period.

To accelerate this release rate and to reduce residual stickiness as found in formulations 3, 4, and 5, mannitol SD100 was changed to crystalline mannitol C50 and used only intra-granularly. Three additional formulations were prepared-Formulations 6, 7, and 8, which are presented in Table 5 above.

Each of formulations 6, 7, and 8 presented no material issues during blending and dry granulation processes, evidencing that these formulations were suitable for use in preparing capsules and tablets as per the claims herein attached.

As to dissolution, FIG. 6 illustrates that the release rate is increased as between the formulation with mannitol SD100 (formulation 4) and mannitol C50 (formulation 6). Moreover, FIG. 7 shows that each of the formulations 6, 7, and 8 all achieved at least 80% release of budiodarone within 1 hour.

D. Change in Capsule

Figure 8:
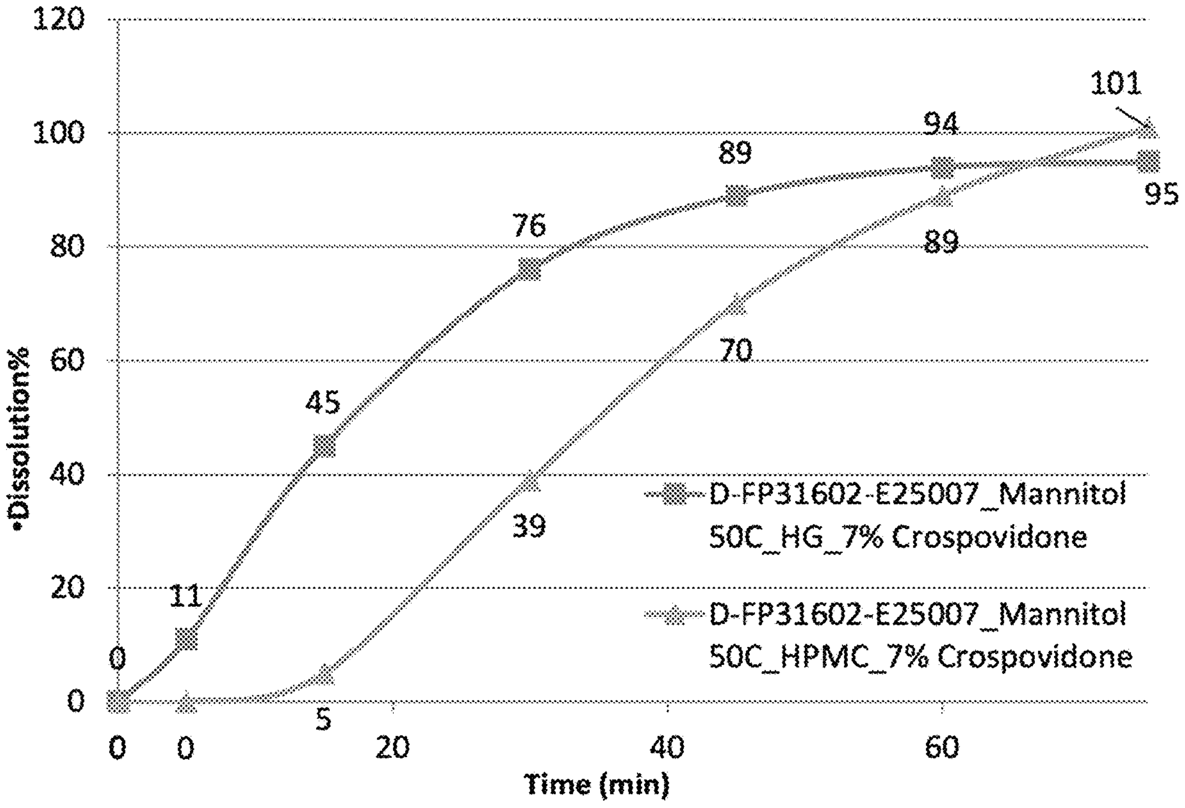
FIG. 8 illustrates the release rates of budiodarone into simulated gastric fluid from two different capsules.

In another experiment, the capsule was changed to a hard gelatin capsule. Formulation 7 was used to test the dissolution rates for an HPMC size 1 capsule and a hard gelatin (HG) size 1 capsule. The results of this test are depicted in FIG. 8. As can be seen from FIG. 8, the unexpected increase in the amount of budiodarone released from the HG capsule in the first 30 minutes during dissolution, as compared to the amount of budiodarone released from an HPMC capsule, was retained from the microcrystalline capsule of Formulation 4. Specifically, at 30 minutes, almost twice the amount of budiodarone (76%) has been released from the HG capsule as compared to 39% released from the HPMC capsule.

Formulations

Based on the teachings herein, including the Examples below, in one embodiment, the formulations described herein comprise:

- a crystalline budiodarone salt such as a mono-tartrate salt, a mono-fumarate salt, and a mono-citrate salt, and preferably a mono-tartrate salt;
- microcrystalline cellulose;
- colloidal silica dioxide
- a sugar alcohol or starch;
- one or more lubricants; and
- a disintegrant or super disintegrant.

In one embodiment, the formulations described herein comprise:

- a crystalline budiodarone mono-tartrate salt;
- microcrystalline cellulose;
- colloidal silica dioxide
- a sugar alcohol;
- one or more lubricants; and
- a disintegrant or super disintegrant.

In the following embodiments (E-1 through E-4), the components described above can be used in formulations described in Table 6 (wherein all percentages are weight percentages) to prepare coated granules.

TABLE 6

| Component | E-1 | E-2 | E-3 | E-4 |
|---|---|---|---|---|
| CBT | about 40-65% | about 45-60% | about 45-55% | about 50-55% |
| MCC | about 20-35% | about 22-32% | about 24-30% | about 25-29% |
| Sugar Alcohol | about 5-20% | about 9-16% | about 10-16% | about 12-15% |
| CDO | about 0.5-1.5% | about 0.6-1.4% | about 0.7-1.25% | about 0.9-1.1% |
| Lubricant-1 | about 0.2-0.8% | about 0.3-0.7% | about 0.4-0.6% | about 0.45-0.55% |
| Lubricant-2 | about 0.2-0.8% | about 0.3-0.7% | about 0.4-0.6% | about 0.45-0.55% |
| SD-1 | about 1.5-6% | about 2-5.5% | about 2-5% | about 2-3% |
| SD-2 | about 1.5-6% | about 2-5.5% | about 2-5% | about 2-3% |
| Total | 100% | 100% | 100% | 100% |

Lubricant 1 is the intra-granular, and Lubricant 2 is the extra-granular lubricant. SD-1 (Super Disintegrant-1) is intra-granular. SD-2 is the extra-granular Super Disintegrant.

In one embodiment in Table 6, the sugar alcohol is mannitol; Lubricant-1 and Lubricant-2 are magnesium stearate; and Super Disintegrant-1 and Super Disintegrant-2 are crosslinked polyvinylpyrrolidone.

The following examples are provided. In these examples, the following terms and abbreviations are defined. Terms and abbreviations not defined have their conventional chemical and pharmaceutical definitions.

| Abbreviation | Meaning |
|---|---|
| AF or AFib | Atrial fibrillation |
| AFB | Atrial fibrillation burden |
| API | Active pharmaceutical ingredient |
| BID or b.i.d. | Bis in die in Latin, twice a day |
| Bonapace automatic filling machine | Dott. Bonapace & C SRL Via Abele Merli 10/A, 20095 Cusano Milanino (MI), Italy |
| CBT | Crystalline budiodarone tartrate form-1 |
| CDO | colloidal silica dioxide, Aerosil 200 Pharma, sold by Evonik Corporation, Parsippany, NJ, USA |
| CK-CL or CKL | crosslinked polyvinylpyrrolidone |
| CL | crosslinked |
| EG | extra-granular or extra-granular |
| Ex. CK-CL | Extra-granular Crospovidone Kollidon CL, sold by BASF USA, Florham Park, New Jersey, USA |
| Ex. Mg Stearate | extra-granular magnesium stearate |
| EXF | Ultrafine particle size |
| FTIR | Fourier Transform Infrared (IR) spectroscopy |
| g | Grams when next to a number |
| HDPE | High-density polyethylene |
| HF | Heart failure |
| HFpEF | Heart failure with preserved ejection fraction |
| HFrEF | Heart failure with reduced ejection fraction |
| HPLC | High-performance Liquid Chromatography |
| HPMC | hydroxypropyl methylcellulose (aka hypomellose) |
| Hydrogenated vegetable oil | Lubritab ® available from JRS Pharma, Holzmuhle 1 D-73494 Rosenberg, Germany |
| IG | intra-granular or intragranular |
| Int. CK-CL | Intra-granular Crospovidone Kollidon CL, sold by BASF USA, Florham Park, New Jersey, USA |
| Int. Mg Stearate | Intra-granular magnesium stearate |
| IPA | Isopropanyl |

-continued

| Abbreviation | Meaning |
|---|---|
| IUPAC | International Union of Pure and Applied Chemistry and is referenced as a system of nomenclature. |
| KF | Karl Fisher method is a titration technique for accurately determining the water content of a sample. |
| Klucel EXF | Hydroxypropyl cellulose sold by Ashland Global Holdings, Wilmington, Delaware, USA |
| Magnesium Stearate | Ligamed MF-2-V-MB |
| MCC | Avicel ® PH - 101 microcrystalline cellulose, sold by Pharma Solutions, Penn Valley, PA, USA |
| mg | milligram |
| min. | minute |
| MW | Molecular Weight |
| NF | National Formulary when used with alginic acid |
| NLT | Not less than when used in reference to chiral purity |
| NMT | Not more than |
| OP | opaque |
| PAF | Paroxysmal atrial fibrillation |
| PVP | polyvinylpyrrolidone |
| RPMs | Rotations Per Minute |
| Rt | Retention Time |
| SD | Spray dried |
| Synthetic gastric fluid used in the dissolution test | Water, pH 4.5 with acetate buffer, and 3% Tween 80; Vessel Temperature 37° C.; 75 rpm for 1 hour; 250 rpm thereafter; HPLC method: isocratic using the USP Apparatus 2 paddle discussed supra |
| USP | United States Pharmacopeia |
| XRD | X-ray diffraction |

Comparative Example A—Crystallization of Budiodarone Tartrate with Isopropanol and Water Amorphous budiodarone tartrate salt was added to isopropanol:water at approximately a 15:1 ratio, forming a suspension. The suspension was heated as per the '912 patent until the budiodarone tartrate salt was dissolved. The solution was then slowly cooled, and crystalline budiodarone tartrate formed. After cooling was complete, the crystalline solids were collected and dried. A sample of the crystalline solids was provided for XRD. The resulting XRD pattern is provided in FIG. 1A.

The crystalline budiodarone tartrate was then analyzed for impurities, which are reported in Table 2 above. Analysis of these impurities are assigned to the mechanisms for production as indicated in Table 2.

In addition to one impurity exceeding 0.15 weight percent (impurity 5), other impurities account for almost 0.30 weight percent. The presence of such impurities is a problem, as most countries have regulatory agencies (e.g., the US FDA) responsible for approving new drug applications. These agencies require (e.g., as part of the drug approval process) that each batch of drug be tested for contaminants (impurities). The FDA, for example, addresses impurities on a tiered scale based on the concentration of the impurity in a representative test sample from each batch of drug made using the scale presented in Table 7 (percents are weight percents):

TABLE 7

| Maximum Daily Dose of Drug | A. Reporting Threshold | B. Identification Threshold | C. Qualification Threshold |
|---|---|---|---|
| g/day | 0.05% | 0.10% or 1.0 mg per day intake (whichever is lower) | 0.15% or 1.0 mg perd ay intake (whichever is lower) |
| 2 g/day | 0.03% | 0.05% | 0.05% |

Table 7 is qualified as follows:

Higher reporting contaminant thresholds should be scientifically justified; and

Lower reporting contaminant thresholds can be appropriate if the impurity is unusually toxic.

Given that the projected dosing of crystalline budiodarone tartrate is up to 600 mg twice a day, the weight percent of impurities for 1, 2, and 5, and the total weight of drug delivered per day pose a problem.

It is proposed that contaminants 1, 2, and 5 were generated directly or indirectly due to the presence of isopropanol in the crystallization solvent and remained in the crystalline product. So it is further contemplated that any attempts to remove these impurities by recrystallization in isopropanol and water could actually increase the load of these impurities.

Comparative Example B—Recrystallization of Budiodarone Tartrate

Recrystallization was considered as an option for removing impurities associated with isopropanol. Careful consideration as to the recrystallization solvent was necessary, as solvent changes can change the polymorph formed or generate a separate set of impurities. Given that isopropanol was a protic solvent, it was considered that protic solvents may be necessary as protic interactions between budiodarone and the protic solvents could be essential for recrystallization. As such, the use of acetonitrile with a minor amount of water was unpredictable based on these considerations.

Nevertheless, recrystallization was undertaken using acetonitrile:water at about a 15:1 ratio. The suspension was heated until solubilization occurred and then cooled. In some embodiments, once crystallization was initiated, the system was reheated to solubilize these crystals, and then crystallization was allowed to proceed to completion. The crystals were collected, and an XRD pattern was generated and provided as FIG. 1B.

Figure 1A:
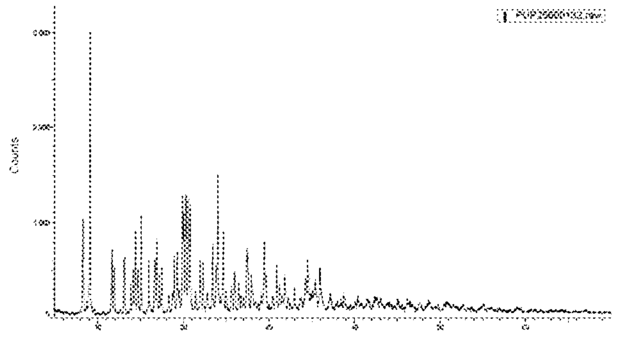
Figure 1B:
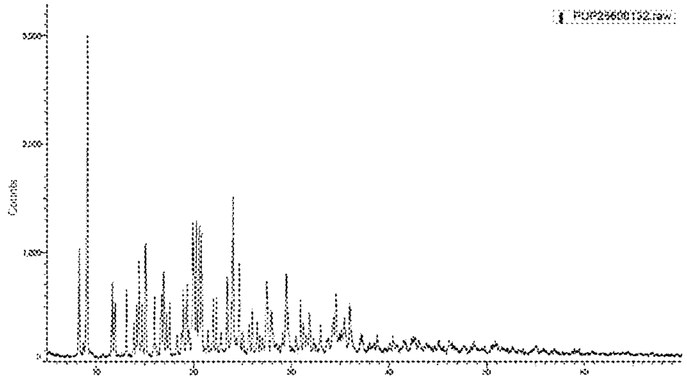
Figure 2:
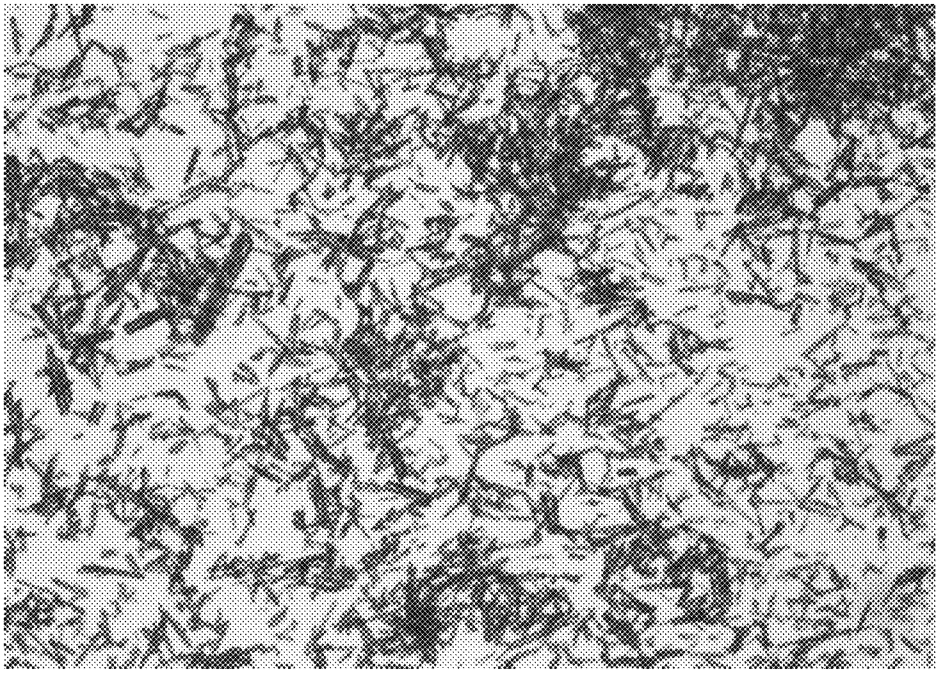
FIG. 2 illustrates that the crystalline structure of budiodarone tartrate Form 1 is short, needle-like crystals that tend to aggregate.

In view of the consistency between FIG. 1A and FIG. 1B, it was concluded that the crystal structure of budiodarone generated by recrystallization was Form-1. Moreover, the purity of the crystalline product was substantially improved with just one impurity present at 0.06 weight percent, as shown in Table 8 below.

A. Co-sifted the budiodarone tartrate salt and the excipients (except for the hydrogenated vegetable oil) listed in Comparative Examples D and E through a 20 mesh screen;

B. Sifted hydrogenated vegetable oil (Lubritab) through a 60 mesh screen;

TABLE 8

| | Structure | Isopropanol | Acetonitrile |
|---|---|---|---|
| Impurity 1<br>Decarboxylate<br>Rt = 14.272 min<br>MW = 602.98 | 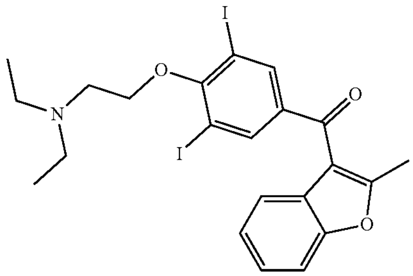 [SMILES: CCN(CC)CCOc1c(I)cc(C(=O)c2c(C)oc3ccccc23)cc1I] | 0.120 weight % | Not present |
| Impurity 2<br>IPA-analogue<br>Rt = 15.418 min<br>MW = 690.00 | 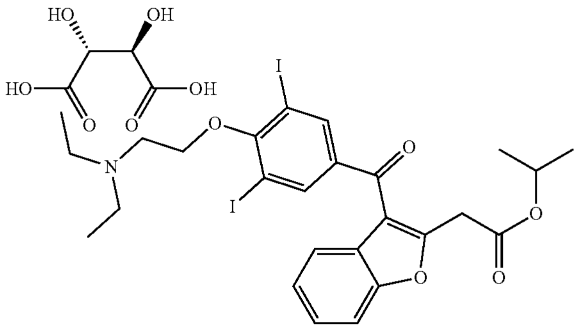 | 0.093 weight % | Not present |
| Impurity 3<br>Unknown 1<br>Rt = 16.134 min | Unknown | 0.036 weight % | Not present* |
| Impurity 4<br>Unknown 2<br>Rt = 17.845 min | Unknown | 0.025 weight % | Not present* |
| Budiodarone impurity | Unknown | | 0.06 weight %<br>* this could be either impurity 3 or 4 above. |
| Impurity 5<br>EL-7<br>Rt = 35.056 min<br>MW = 604.17 | 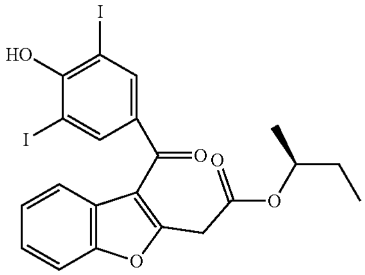 [SMILES: CC[C@H](C)OC(=O)Cc1oc2ccccc2c1C(=O)c1cc(I)c(O)c(I)c1] | 0.167 weight % | Not present |
| Total | | 0.441 weight % | 0.06 weight % |

Surprisingly, the acetonitrile:water co-solvent did not generate any amount of impurities 1, 2, and 5. This suggests that heating of the crystallization solvent by itself is not a source of these impurities, but rather the isopropanol is assisting in both decarboxylation and elimination.

Comparative Example C—Formulation Preparation for Comparative Examples D and E Formulations for capsules and tablets in Comparative Examples D and E were conducted as follows:

C. Loaded the sifted material from A into a tubular bin and mixed at 46 RPMs for 10 minutes;

D. Unload powder mixture and sift through a 20 mesh screen;

E. Repeat the blending process by mixing at 46 RPMs for 3 minutes;

F. The sifted hydrogenated vegetable oil was transferred to the tubular bin and mixed at 46 RPMs for 3 minutes.

G. Encapsulation was tried using HPMC capsules size “0” and a Bonapace automatic filling machine, available from Techceuticals Inc., Cleveland, OH, USA.

With the exception that an additional additive was used in the excipients in Comparative Example D as compared to Comparative Example C, resulting in different percentages. Any of the listed excipients in Examples C and D can be used as extra-granular excipients when preparing a tablet or capsule.

Comparative Example D—Failure of Formulation 1 in Capsules and Tablets

Formulation 1 was prepared as found in Table 9. It contains a glidant and a lubricant, and Formulation 1 was tested for use in a capsule:

TABLE 9

| Component | Formulation 1 |
|---|---|
| Crystalline budiodarone tartrate | 58.85 g |
| Crosslinked polyvinylpyrrolidone | 5.00 g |
| Microcrystalline Cellulose | 33.68 g |
| Talc | 0.50 g |
| hydrogenated vegetable oil | 2.00 g |
| TOTAL | *100.03 g |

*Note: component masses do not add up to exactly 100 g due to rounding.

Upon preparation, Formulation 1 had poor flowability in the blender. As shown in FIG. 3, the composition stuck to the walls of the blender bin, which was due to agglomeration. Of the 100 capsules prepared for testing, 81 were deemed failures due to agglomeration issues. This formulation could not support the encapsulation process using a Bonapace machine. This formulation was discarded for capsule manufacture.

As to tablet formation, Formulation 1 was tested for use in preparing tablets using a manual die filling. As shown in FIG. 4, a large amount of material adhered to the punch after approximately 8 compression steps, rendering this method unfeasible. This formulation was discarded for tablet manufacture.

Comparative Example D—Failure of Formulation 2

Formulation 2 was prepared as found in Table 10. It contains a glidant and a lubricant and further contains hydroxypropyl cellulose.

TABLE 10

| Component | Formulation 2 | Weight Percent for 100 g |
|---|---|---|
| CBT Form-1 | 47.62 g | |
| Crosslinkedpolyvinylpyrrolidone | 6.00 g | |
| Microcrystalline Cellulose | 39.88 g | |
| Talc | 0.50 g | |
| Hydrogenated vegetable (cottonseed )oil | 2.00 g | Lubritab |
| Hydroxypropyl cellulose | 4.00 | Klucel EXFR |
| Total | 100 g | |

Upon preparation, the composition had poor flowability in the blender and could not support the encapsulation process using a Bonapace machine. This formulation was discarded as a failure.

Example 1—Comparison of the Properties of Three Different Formulations

Three different formulations were prepared, with each having the following components as shown below in Table 11 (all percentages are weight percentages):

TABLE 11

| | Formulation 3 | Formulation 4 | Formulation 5 |
|---|---|---|---|
| CBT Form-1 | 52.63% | 52.63% | 52.63% |
| MCC | 40.37% | 26.91% | 26.91% |
| IG Mannitol 100SD | 0 | 13.46% | 0 |
| EG Mannitol 100SD | 0 | 0 | 13.46% |
| CDO | 1.00% | 1.00% | 1.00% |
| Int. Mg Stearate | 0.50% | 0.50% | 0.50% |
| Ex. Mg Stearate | 0.50% | 0.50% | 0.50% |
| Int. CKL | 2.50% | 2.50% | 2.50% |
| Ex. CKL | 2.50% | 2.50% | 2.50% |
| Total | 100% | 100% | 100% |

Example 2—Preparation Methods for Formulations 3, 4, and 5

Formulations 3, 4, and 5 were prepared as follows:

A. Co-sifted crystalline budiodarone tartrate salt and the excipients other than the magnesium stearate (and only when mannitol is used) through a 20 mesh screen;
B. Sifted magnesium stearate through a 60 mesh screen;
C. Loaded the sifted material from A into a blender bin and mixed at 15 RPMs for 10 minutes;
D. Unload powder mixture and sift through a 20 mesh screen;
E. Repeat the blending process by mixing at 15 RPMs for 5 minutes;
F. The sifted magnesium stearate was transferred to the blender bin and mixed at 15 RPMs for 5 minutes.
G. The pre-lubricated powder mixture was used to make granules using the TF-Labo machine at 3 Mpa pressure, followed by sifting through an 18 mesh screen.
H. The granules produced above were then coated with extra-granular crosslinked polyvinylpyrrolidone (CKL) and extra-granular mannitol 100SD, which were then sifted as per step A above and then transferred to the blender bin and mixed at 15 RPMs for 5 minutes.
I. The sifted extra-granular magnesium stearate was transferred to the blender bin and mixed at 15 RPMs for 5 minutes.

These formulations still had a slight sticking issue that was observed on the surface of the blender bin during the blending process in the three trials. In addition, there was observed a slight material sticking issue was observed on the roller during the dry granulation process in the three trials. Nevertheless, the powder blend exhibited good flowability to support the encapsulation process in the three trials, which was all that was required at this time.

Example 3—Capsule Performance for Formulations 3, 4, and 5

A multiplicity of HPMC capsules were used, weighing on average 77.9 mg. Each capsule was set to receive 360 mg of granules. The capsules were split among the three formulations, using 10 capsules in each formulation to assess relative variations in the total weight of the finished capsule.

Additionally, a total of 50 capsules were evaluated for each formulation, with a pass or fail designation. In Table 12 below, the variance in total weight of the finished capsules is reported, as is the number of passes and failures.

TABLE 12

| | Formulation 3 | Formulation 4 | Formulation 5 |
|---|---|---|---|
| Total average weight of the capsule | 459.52 mg | 457.15 mg | 459.5 mg |
| Average Variance (limit 5%) | 1.91% | 1.85% | 1.77% |
| Pass rate | 45/50 = 90% | 45/50 = 90% | 46/50 = 92% |

In addition, the average rate of dissolution for capsules (excluding failures) was evaluated. The test proceeded using simulated gastric fluid and test conditions provided in the table of abbreviations above. In order to pass this test, at least 80% of the active (budiodarone) must be released from the capsule within 1 hour.

The results of this test are presented in FIG. 10. It was noted that some material sticking was observed on the sinkers in the first 30 min., which was then resolved. In addition, each of Formulations 3, 4, and 5 passed the dissolution test with what was considered to be marginal pass results. So, it was decided that changes to the formulations should be considered.

Example 4—Evaluating the Replacement of Mannitol 100SD with Mannitol 50C in Varying Amounts of Crosslinked Polyvinylpyrrolidone This example evaluates the impact of replacing spray-dried mannitol, mannitol 100SD, with mannitol 50C at various crosslinked polyvinylpyrrolidone concentrations in the granules made as per Example 2. Table 5 supra shows the relative content of each of the formulations 6, 7, and 8.

Example 5—Capsule Performance for Formulations 6, 7, and 8

A multiplicity of HPMC capsules was used, weighing on average 78.2 mg. Each capsule was set to receive 360 mg of granules. The capsules were divided among the three formulations, with 10 capsules in each formulation, to assess relative variations in the total weight of the finished capsules. In addition, a total of 50 capsules were evaluated for each formulation as passing or failing. In Table 12 below, the variance in total weight of the finished capsules is reported, as is the number of passes and failures.

TABLE 13

| | Formulation 6 | Formulation 7 | Formulation 8 |
|---|---|---|---|
| Total average weight of the capsule | 456.05 mg | 452.21 mg | 457.58 mg |
| Average Variance (limit 5%) | 1.43% | 1.24% | 1.47% |
| Pass rate | 46/50 = 92% | 18/20 = 90% | 47/50 = 92% |

In addition, the average rate of dissolution for capsules (excluding failures) was evaluated. The test proceeded using simulated gastric fluid and test conditions provided in the table of abbreviations above. In order to pass this test, at least 80% of the active (budiodarone) must be released from the capsule within 1 hour.

The results of this test are presented in FIG. 7. All formulations passed the 80% within 1 hour test. However, there were two surprising results. First, the variable amount of super disintegrant used in these formulations showed a result that was contrary to expectations. Specifically, the best results were achieved using the least amount of crospovidone (the super disintegrant), suggesting that the addition of super disintegrant above about 5 or 6% by weight did not provide any benefits in increasing the dissolution speed.

Next, the dissolution results of formulations 4 and 6 were compared. These two formulations are identical except that Formulation 4 uses spray-dried mannitol 100SD, whereas Formulation 6 uses crystalline mannitol 50C. FIG. 6 demonstrates that Formulation 6, which contains crystalline mannitol 50C, releases significantly more, almost double the amount of, budiodarone during the first 30 minutes as compared to Formulation 4. This is also contrary to the literature, which teaches that spray-dried mannitol is better for increasing the release rates of a drug as compared to crystalline mannitol.

Example 6—Capsule Performance Comparison for Formulation 7 with a Different Capsule Shell The test conducted in Example 6 above was repeated, except that formulation 7 was placed into a hard gelatin shell and tested for dissolution. These results were then compared to those found in Example 6 for formulation 7, which used a microcrystalline cellulose-based capsule. The results of this test are found in FIG. 8, which shows a significant and unexpected increase where about 76% of the budiodarone is released from the capsule in about 30 minutes in the hard gelatin capsule. Again, the differential between the amount of budiodarone released using crystalline mannitol 50C compared to spray-dried mannitol 100 SD remains approximately doubled.

Example 7-Preparation of Formulation 9

A formulation was prepared in the manner described in Example 2 and having the following components as shown below in Table 14 (all percentages are weight percentages):

TABLE 14

| Material | mg/tablet | Formulation 10 % (w/w) | Actual Qty/ Batch (g) |
|---|---|---|---|
| Intra-granular excipients | | | |
| ATI-2042 | 200.00 | 64.34* | 965.2 |
| Mannitol 50C | 51.15 | 9.55* | 143.3 |
| Microcrystalline Cellulose PH-101 | 102.25 | 19.11* | 286.5 |
| Crospovidone Kollidon CL | 9.50 | 2.50 | 37.5 |
| Colloidal Silica Dioxide Aerosil 200 Pharma | 3.80 | 1.00 | 15.0 |
| Magnesium Stearate LIGAMED MF-2-V-MB | 1.90 | 0.50 | 7.5 |
| Extra-granular excipients | | | |
| Crospovidone Kollidon CL | 9.50 | 2.50 | 37.5 |
| Magnesium Stearate LIGAMED MF-2-V-MB | 1.90 | 0.50 | 7.50 |
| Vacant Gelatin Capsules Size 1 White OP Cap & Body 44.801 | 1 EA | 1500 EA | 3000 EA |
| Total | 380.00 | 100.00 | — |
| HDPE Bottles for Oral Solid Preparation B100-3 | 1 EA | | 18 EA |

TABLE 14-continued

| Material | mg/tablet | Formulation 10 % (w/w) | Actual Qty/ Batch (g) |
|---|---|---|---|
| Oral Solid Preparation HDPE/PP Child-Resistant Assemble Closure CRC38-1 | | 1 EA | 18 A |

*According to the CoA, the assay as free base of ATI-2042 is 81.8%. For 200 mg strength capsules, actual batch formula % w/w = theoretical batch formula % w/w of API/assay = 52.63/81.8% = 64.34%. The quantity of microcrystalline cellulose PH-101 and mannitol was adjusted with a ratio of 2:1 to compensate for the weight change due to API potency calculation.

Figure 9:
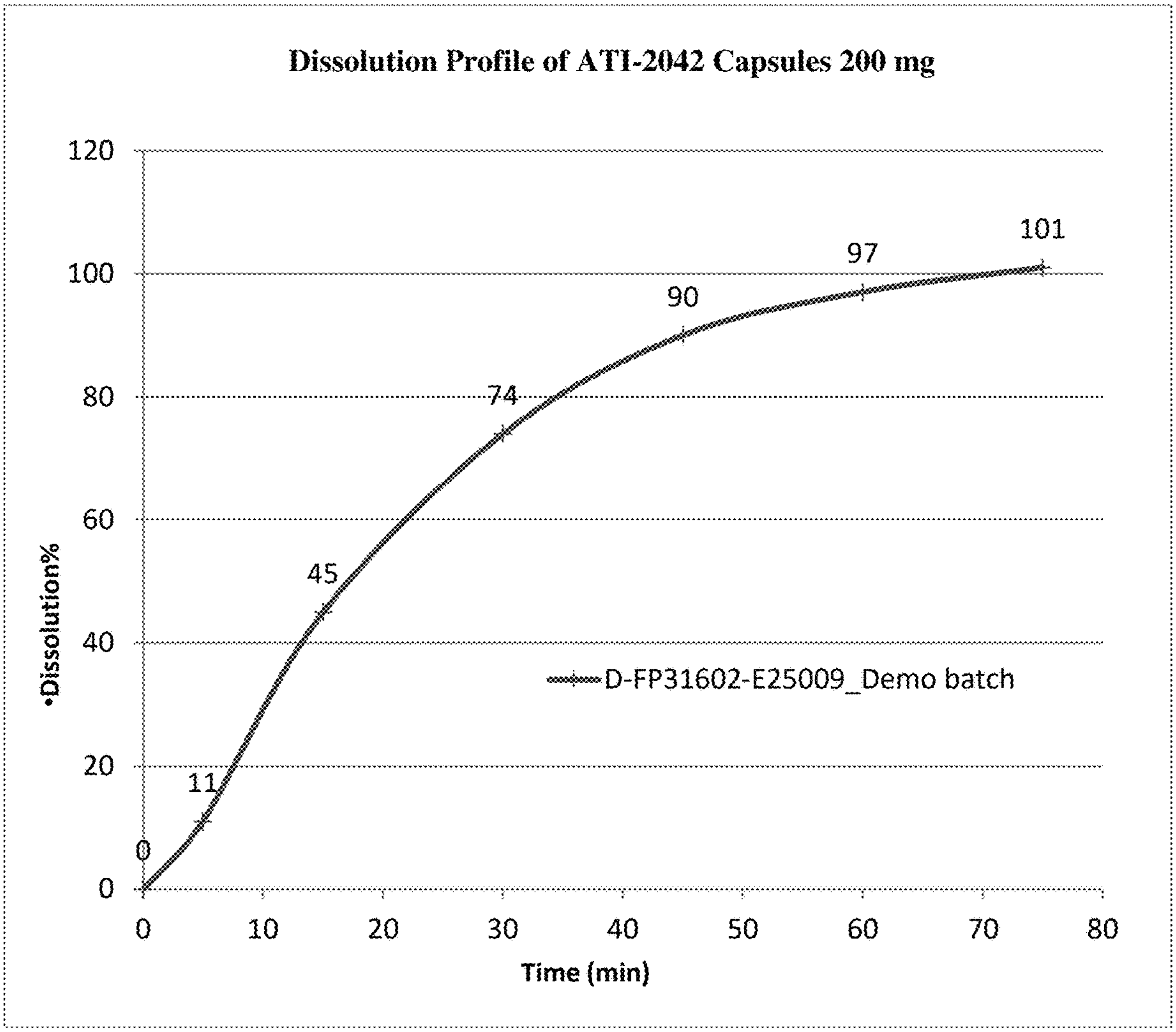
FIG. 9 illustrates the release rate of budiodarone into simulated gastric fluid from a capsule containing 200 mg of budiodarone tartrate.

The test conducted in Example 6 above was repeated, except that formulation 10 was placed into a hard gelatin shell. The results of this test are found in FIG. 9, which shows that changing from mannitol 100SD to mannitol 50C in HPMC capsules increased the release by 1.472-fold at 30 minutes (36% vs 53%). Changing to hard gelatin (HG) capsules with mannitol 50 increased it by another 1.434-fold (53% vs 76%) at 30 minutes. The total increase is 2.1-fold (36% vs 76%).

In one embodiment, the compositions described herein are stored at a temperature of about 25° C. or less, and preferably between about 10° C. and about 25° C.

What is claimed is:

1. A granular formulation of a crystalline budiodarone tartrate salt which comprises an effective amount of the crystalline budiodarone tartrate salt, a microcrystalline cellulose, an effective amount of a sugar alcohol, one or more lubricants, and a disintegrant or a super disintegrant, wherein over 80% of budiodarone is released from the granular formulation within 60 minutes and wherein the crystalline budiodarone tartrate salt has a structure characterized by an X-ray diffraction (XRD) pattern consistent with an XRD pattern of FIG. 1A or FIG. 1B.

2. The granular formulation of claim 1, wherein the crystalline budiodarone tartrate salt employed in the granular formulation comprises a budiodarone salt that is a mono-tartrate salt.

3. The granular formulation of claim 1, wherein said crystalline budiodarone tartrate salt is a mono-tartrate salt whose crystalline structure is characterized by the XRD pattern of FIG. 1A.

4. The granular formulation of claim 1, wherein granules in the granular formulation further comprise an extra-granular lubricant coating.

5. The granular formulation of claim 1, wherein the sugar alcohol is intra-granular.

6. The granular formulation of claim 1, wherein the sugar alcohol is incorporated into an extra-granular lubricant coating.

7. The granular formulation of claim 1, wherein the sugar alcohol is intra-granular and also is part of an extra-granular lubricant coating.

8. The granular formulation of claim 1, wherein the sugar alcohol has 3 to 7 carbon atoms.

9. The granular formulation of claim 8, wherein the sugar alcohol has 5 to 6 carbon atoms.

10. The granular formulation of claim 9, wherein the sugar alcohol is selected from mannitol, sorbitol, or xylitol.

11. The granular formulation of claim 1, wherein the sugar alcohol is a mannitol.

12. The granular formulation of claim 1, wherein said granular formulation comprises a microcrystalline cellulose, crystalline mannitol, magnesium stearate, colloidal silica dioxide, and a crosslinked polyvinylpyrrolidone disintegrant.

13. The granular formulation of claim 1, wherein said granular formulation comprises an extra-granular coating.

14. The granular formulation of claim 13, wherein said extra-granular coating comprises one or both of a lubricant and a disintegrant.

15. The granular formulation of claim 1, wherein said sugar alcohol has an average particle size of about 100 μm or less, preferably 50 μm or less.

16. The granular formulation of claim 1, wherein said granular formulation is prepared by dry granulation.

17. The granular formulation of claim 1, wherein said sugar alcohol has a specific surface area of about 0.5 $m^2/g$ or higher.

18. The granular formulation of claim 1, wherein said granular formulation is incorporated into a capsule.

19. The granular formulation of claim 18, wherein said capsule comprises either a plant-based shell or a gelatinous shell.

20. The granular formulation of claim 19, wherein said plant-based shell comprises microcrystalline cellulose.

21. The granular formulation of claim 19, wherein said capsule is a gelatinous capsule.

22. The granular formulation of claim 1, wherein said granular formulation is incorporated into a tablet.

23. The granular formulation of any one of claims 19 to 21, wherein said capsule includes small laser-generated openings.

24. A method for enhancing dissolution of budiodarone tartrate from a capsule comprising a formulation containing spray-dried mannitol, which method comprises replacing said spray-dried mannitol with mannitol 50C.

25. The granular formulation of claim 1, wherein the sugar alcohol is mannitol 50C.

26. The granular formulation of claim 14, wherein said disintegrant is polyvinylpyrrolidone.

* * * * *